(12) United States Patent
Tol et al.

(10) Patent No.: US 9,744,352 B2
(45) Date of Patent: Aug. 29, 2017

(54) ELECTRONIC MODULE WITH ELECTROMAGNETIC INTERFERENCE PROTECTION

(71) Applicant: MEDTRONIC BAKKEN RESEARCH CENTER B.V., Maastricht (NL)

(72) Inventors: Jeroen Jacob Arnold Tol, Eindhoven (NL); Egbertus Johannes Maria Bakker, Wijk en aalburg (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days.

(21) Appl. No.: 14/952,848

(22) Filed: Nov. 25, 2015

(65) Prior Publication Data

US 2016/0144168 A1 May 26, 2016

Related U.S. Application Data

(60) Provisional application No. 62/084,420, filed on Nov. 25, 2014.

(51) Int. Cl.
| | |
|---|---|
| *A61N 1/00* | (2006.01) |
| *A61N 1/08* | (2006.01) |
| *A61N 1/37* | (2006.01) |
| *G01R 33/28* | (2006.01) |
| *A61N 1/05* | (2006.01) |
| *A61N 1/375* | (2006.01) |
| *G01R 33/36* | (2006.01) |

(52) U.S. Cl.
CPC ............. *A61N 1/08* (2013.01); *A61N 1/3718* (2013.01); *G01R 33/288* (2013.01); *A61N 1/0534* (2013.01); *A61N 1/3754* (2013.01); *G01R 33/3685* (2013.01)

(58) Field of Classification Search
CPC ..... A61N 1/3718; A61N 1/08; A61N 2001/08
See application file for complete search history.

(56) References Cited

U.S. PATENT DOCUMENTS

| | | |
|---|---|---|
| 4,021,759 A | 5/1977 | Campi |
| 5,591,218 A | 1/1997 | Jacobson |
| 6,925,328 B2 | 8/2005 | Foster et al. |
| | (Continued) | |

FOREIGN PATENT DOCUMENTS

WO 2010055453 A1 5/2010

*Primary Examiner* — Scott Getzow
(74) *Attorney, Agent, or Firm* — Shumaker & Sieffert, P.A.

(57) ABSTRACT

Various examples provide devices, systems, and techniques for dissipating electromagnetic interference (EMI) induced energy in a medical device. In one example, an implantable electronic device includes a housing, at least one connector coupled to the housing and configured to at least one of receive first electrical signals or transmit second electrical signals, and an integrated circuit disposed within the housing, wherein the integrated circuit comprises at least one clamp stage coupled to a supply line of the integrated circuit, and wherein the at least one clamp stage is configured to dissipate magnetic resonance imaging (MRI) induced energy from the supply line in response to at least one of a voltage or a current on the supply line exceeding a respective predetermined voltage threshold value or a current threshold value.

35 Claims, 11 Drawing Sheets

(56) References Cited

U.S. PATENT DOCUMENTS

| | | |
|---|---|---|
| 7,941,202 B2 | 5/2011 | Hetke et al. |
| 7,966,075 B2 † | 6/2011 | Johnson |
| 8,600,519 B2 | 12/2013 | Stevenson et al. |
| 8,788,057 B2 * | 7/2014 | Stevenson .............. A61N 1/025 607/116 |
| 2002/0072769 A1 * | 6/2002 | Silvian .................... A61N 1/08 607/2 |
| 2009/0132007 A1 | 5/2009 | Snitting |
| 2010/0208397 A1 * | 8/2010 | Johnson .................. A61N 1/08 361/54 |
| 2013/0110203 A1 | 5/2013 | Dronov et al. |
| 2014/0022678 A1 * | 1/2014 | Maile ...................... H02H 3/20 361/56 |

\* cited by examiner
† cited by third party

ELECTRONIC MODULE WITH ELECTROMAGNETIC INTERFERENCE PROTECTION

This application claims priority to U.S. Provisional Patent Application No. 62/084,420, entitled "AN ELECTRONIC MODULE FOR A SYSTEM FOR NEURAL APPLICATIONS WITH HIGH EMI PROTECTION" and filed Nov. 25, 2014, the entire contents of which is incorporated herein by reference.

TECHNICAL FIELD

The disclosure relates to implantable medical systems and, more particularly, implantable medical systems for limiting electromagnetic interference.

BACKGROUND

Implantable neurostimulation devices have been used to treat acute or chronic neurological conditions. Deep brain stimulation (DBS), the mild electrical stimulation of subcortical structures, belongs to this category of implantable devices and has been shown to be therapeutically effective for Parkinson's disease, Dystonia, Essential Tremor, Obsessive Compulsive Disorder, and Epilepsy. New applications of DBS in the domain of psychiatric disorders (clinical depression, anorexia nervosa, schizophrenia) are being researched. In existing systems, a lead carrying four ring electrodes at its tip is connected to an implantable pulse generator.

SUMMARY

In general, the disclosure describes techniques, devices, and systems for dissipating current in a medical device that has been induced by electromagnetic interference (EMI), such as during exposure to Magnetic Resonance Imaging (MRI) gradient fields. An electronic module may include an integrated circuit that includes one or more clamps coupled to one or more power supply domains. When excess current is generated on the supply domains, the one or more clamps may operate to absorb the excess energy instead of allowing the current to flow to other components of the integrated circuit. In some examples, the integrated circuit may include a clamp configured to absorb energy from a low voltage supply domain and another clamp configured to absorb energy from a high voltage supply domain. One or more clamps may be switched off during normal medical device operation to reduce the power load and allow the integrated circuit to operate under a low power consumption design.

In one example, the disclosure is directed to an implantable electronic device that includes a housing, at least one connector coupled to the housing and configured to at least one of receive first electrical signals or transmit second electrical signals, and an integrated circuit disposed within the housing, wherein the integrated circuit comprises at least one clamp stage coupled to a supply line of the integrated circuit, and wherein the at least one clamp stage is configured to dissipate magnetic resonance imaging (MRI) induced energy from the supply line in response to at least one of a voltage or a current on the supply line exceeding a respective predetermined voltage threshold value or a current threshold value.

In another example, the disclosure is directed to a system that includes a first electronic module comprising a first housing, a second electronic module comprising a second housing distinct from the first housing, a first connector coupled to the first housing and configured to at least one of receive first electrical signals from or transmit second electrical signals to the first electronic module, an integrated circuit disposed within the second housing, wherein the integrated circuit comprises at least one clamp stage coupled to a supply line of the integrated circuit, and wherein the clamp stage is configured to dissipate magnetic resonance imaging (MRI) induced energy from the supply line in response to at least one of a voltage or a current on the supply line exceeding a respective predetermined voltage threshold value or a current threshold value, and a second connector, and a medical lead comprising a plurality of electrodes and configured to be electrically coupled to the second electronic module via the second connector.

In another example, the disclosure is directed to a system that includes means for receiving first electrical signals from a first electronic module comprising a first housing and by a second electrical module comprising a second housing distinct from the first housing, and an integrated circuit within the second housing of the second electrical modules, wherein the integrated circuit comprises means for supplying a voltage for the integrated circuit, means for providing a ground for the integrated circuit, and means for, responsive to at least one of a voltage or a current on the means for supplying the voltage exceeding a respective predetermined voltage threshold value or a current threshold value, dissipating magnetic resonance imaging (MRI) induced energy from the means for supplying the voltage, wherein the means for dissipating the MRI induced energy is coupled between the means for supplying the voltage and the means for providing the ground.

The details of one or more examples are set forth in the accompanying drawings and the description below. Other features, objects, and advantages of the disclosure will be apparent from the description and drawings, and from the claims.

DETAILED DESCRIPTION

Figure 1:
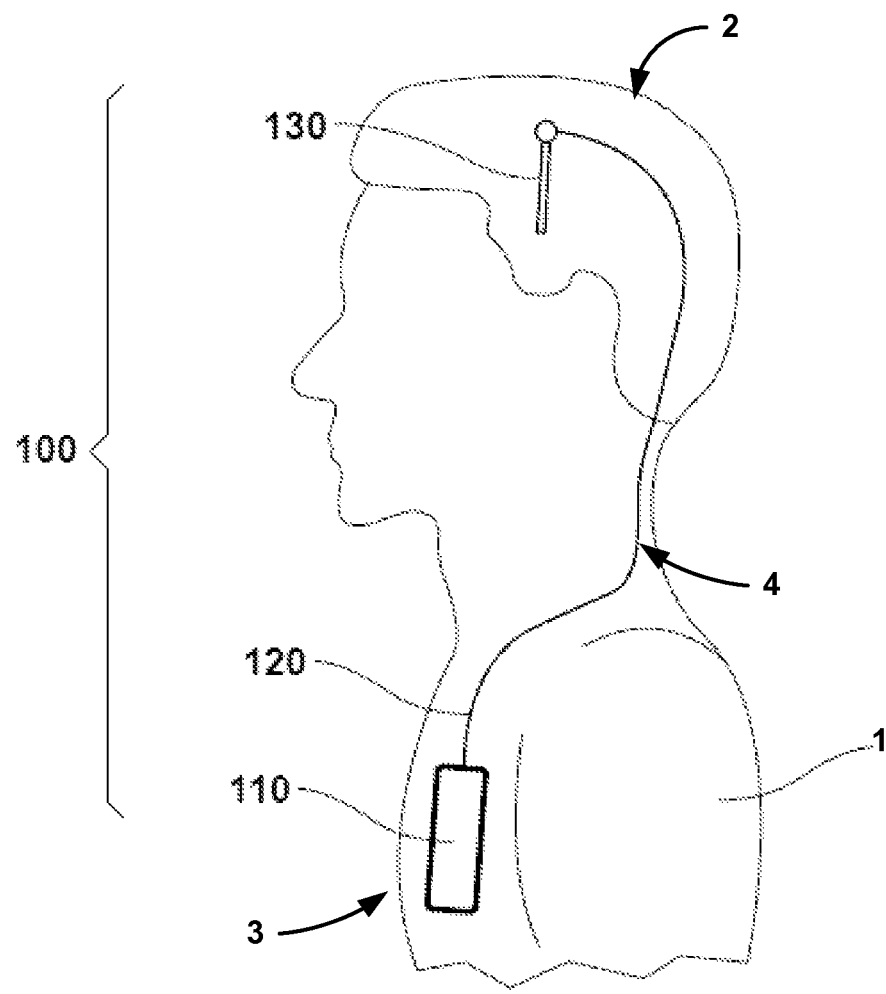
FIG. 1 is a conceptual drawing of an example neurostimulation system that delivers deep brain stimulation (DBS) according to the present disclosure.

This disclosure is related to devices, systems, and techniques related to dissipating EMI induced energy from circuitry of a medical device. In some examples, these devices, systems, and techniques may include one or more electronic modules for a system for neural applications, such as neurorecording and/or neurostimulation. Neural applications may include deep brain stimulation or spinal cord stimulation, for example. The one or more electronic modules may include an active lead can element and/or a controller. Each of these electronic modules may be distinct from each other and provide various functions for the system.

Some systems include smaller electrodes using a technology based on thin film manufacturing. These systems consist of a medical lead made from a thin film based on thin film technology, as, e.g., described in WO 2010/055453 A1, which is hereby incorporated by reference in its entirety. The thin film may be configured to carry multiple electrodes such that the distal tip of the thin film can be covered with an array of electrodes. The thin film may then be assembled into a lead. Such leads may enhance the precision available to address the appropriate target in the brain and relax the requirements of positioning during implantation. This increased precision available using multiple electrodes may allow stimulation therapy to reduce undesired side effects caused by undesired stimulation of neighboring areas. Leads that are based on thin film manufacturing are disclosed by U.S. Pat. No. 7,941,202 and have been used in research products in animal studies. U.S. Pat. No. 7,941,202 is hereby incorporated by reference in its entirety.

In existing systems, a deep brain stimulation (DBS) lead has, for example, four 1.5 mm-wide cylindrical electrodes at the distal end of a lead spaced by 0.5 mm or 1.5 mm. The diameter of the lead may be approximately 1.27 mm and the metal used for the electrodes and the interconnect wires is typically an alloy of platinum and iridium. The coiled interconnect wires may be insulated individually by a fluoropolymer coating and protected in a urethane tubing of a few tens of microns thick. With such electrode design, electrical current distribution may emanate uniformly around the circumference of the electrode which results in stimulation of all areas surrounding the electrode.

The lack of fine spatial control over current and electric field distributions using such typical electrodes implies that stimulation can easily spread into adjacent structures inducing adverse side-effects in as much as 30% of the patients. To overcome this problem, systems with high density electrode arrays can provide the ability to steer, or direct, the stimulation field to the appropriate anatomical target (hence the term steering brain stimulation). The clinical benefit of DBS may be largely dependent on the spatial distribution of the stimulation field in relation to brain anatomy. To improve therapeutic benefits while avoiding unwanted side-effects, systems should provide precise control over the location of the stimulation field.

Stimulation with existing DBS leads may be performed using monopolar, bipolar, or even multipolar stimulation. Neurostimulation devices with steering brain stimulation capabilities can have a large number of electrode contacts (e.g., n>10) that can be connected to electrical circuits such as current sources and/or a system ground. Stimulation may be considered monopolar when the distance between the anode and cathode is several times larger than the distance of the cathode to the stimulation target. During monopolar stimulation in homogeneous tissue, the electric field may be distributed roughly spherical similar to the field from a point source. When the anode is located close to the cathode, the distribution of the field becomes more directed in the anode-cathode direction. As a result of this closer location, the field can get stronger and neurons are more likely to be activated in this area due to a higher field gradient.

Although the exact mechanisms of DBS for therapy are unknown, it is hypothesized that polarization (de- and/or hyperpolarization) of neural tissue is likely to play a prominent role both for suppression of clinical symptoms and for induction of stimulation-induced side-effects. Since a neuron must be depolarized to be activated, neurons are depolarized more easily when they are closer to the cathode than by the anode (e.g., about 3-7 times more depending on type of neuron, etc.).

DBS leads are typically implanted via a stereotactic neurosurgical procedure. The planning of a stereotactic procedure involves the identification of the DBS target (e.g. the subthalamic nucleus) on the basis of MR (Magnetic Resonance; also referred to as MRI=Magnetic Resonance Imaging) or CT (Computed Tomography; also referred to as CTA=Computed Tomography Angiography) images of the patient's head/brain and defining a point within the target nucleus. A stereotactic planning station (e.g. a computer system) may provide the stereotactic coordinates of the target point. The stereotactic coordinates can be referenced externally and thus be used by a physician in an operating room to precisely navigate the DBS lead to the selected point in the brain.

Reducing the size of components in a DBS system, such as an implantable pulse generator, an active lead can element (e.g., an electronic module separate from the implantable pulse generator), and other electronic parts of a DBS system may be desirable to limit displacement of patient tissue, provide a less noticeable implant for the patient, and otherwise reduce the clinical impact of the implanted system. The active lead can element may be configured of a smaller size in order to reduce its clinical impact, such as reduce skin erosion that occurs when the active lead can element is mounted on a patient's cranium. The implantable pulse generator (e.g., an electronic module different from the active lead can) may also be constructed with smaller dimensions and/or limited weight. Smaller dimensions of the implantable pulse generator may increase patient comfort by being less noticeable under the skin and reduce the risk of displacement that can be caused by larger and heavier devices. However, the dimensions of the implantable pulse generator may still be large enough to house a battery that provides sufficient operational capacity.

In existing implanted electronic systems, any electromagnetic interference (EMI) must be limited and kept outside of the area of the module that includes vulnerable electronic components to prevent damage caused by higher currents and/or voltage and/or to prevent interference with normal operation of the system. However, typical approaches for handling EMI currents require components that take up a large volume of the electronic module. Therefore, the electronic module must be made larger than desired or fewer operational components can be included in the electronic module to maintain a desired size of the electronic module.

In one example, when a patient with an implanted electrical system undergoes MR imaging, strong radio frequency (RF) and gradient fields of the MRI machine induce excess current and overvoltage on the implant's electronics. This impact is even more severe when the implant has cables and/or leads attached to it such as in a deep brain stimulation system. Therefore, the system can include protection to prevent or minimize high current and/or voltages induced by the MRI machine that could otherwise damage the implant's electronic components.

Magnetic fields of MRI machines can be in the range from 0.2 Tesla up to more than 10 Tesla. Commonly used MRI machines intended for human imaging have magnetic fields between 1.0 Tesla and 1.5 Tesla. RF and gradient fields from the MRI machine may cause EMI and induce currents and/or voltages within a medical device.

Typically, implanted electronics can protect circuitry from strong electromagnetic interference (EMI) of an MRI machine by having a Faraday cage-like construction formed by, for example, a titanium enclosure penetrated by feedthrough pins. Each pin may include its own protection, for example, by way of a large capacitor on each feedthrough pin as an integral part of the conductive housing itself. However, when an implanted device has many feedthrough pins and/or a large pin density, it may not be feasible to provide large capacitors for each of the feedthrough pins as a protection measure against, for example, MRI induced currents. In one example, the capacitors may require a large volume that increases the size of the electronic module and/or other functional components may need to be removed from the module in order to maintain a desired volume of the module. In other words, integration of a capacitor large enough on each feedthrough pin of the active lead can module may consume too much space in the module and lead to a large module of unacceptable size. Alternatively, or in addition, the application of protection diodes on all feedthrough pins may also take of a large volume of the implant and/or result in unwanted stimulation from electrodes of the implant due to the rectification of the MRI induced electrical waveforms.

As described herein, an electronic module for an implantable medical system may provide components configured to protect electrical circuitry (e.g., one or more integrated circuits) from EMI induced currents such as currents generated due to MRI systems. The electrical module may be used as or part of an implantable medical system configured for neural applications such as neurostimulation and/or neurorecording. In some examples, the implantable medical system may be configured to generate and deliver deep brain stimulation (DBS) therapy, spinal cord stimulation therapy, or therapy to other tissues of a patient.

In some examples, the electronic module may be described as an active lead can element that may be or a part of an implantable medical system configured to provide neurostimulation and/or neurorecording. Implementation of the EMI dissipation techniques described herein, such as incorporating one or more clamps on an integrated circuit of the active lead can element may result in a reduced volume of the active lead can element compared to an element that would otherwise include large capacitors on each feedthrough pin.

In one example, an electronic module (e.g., the active lead can element) for an implantable medical system is described as including a housing, at least one connector arranged at the housing of the module for supplying electrical signals to and/or receiving signals from the electronic module, and an integrated circuit. The electronic module may be coupled to another distinct electronic module having its own housing and/or one or more medical leads carrying one or more electrodes. The integrated circuit may include a semiconductor integrated circuit which is arranged inside of the housing of the electronic module. The integrated circuit may, in some examples, be an application specific integrated circuit (ASIC).

In some examples, the electronic module may also include at least one direct current (DC) blocking element inside the housing and coupled between the connector and a bond pad of the integrated circuit. In some examples, the integrated circuit may include at least one clamp stage integrated in the integrated circuit and coupled between a supply line (e.g., a supply voltage line) and a system ground line of the integrated circuit. In other examples, the at least one clamp stage of the integrated circuit may be coupled between a first supply line and a second supply line where the first supply line has a voltage or current different (e.g., a higher voltage) than the second supply line. The clamp stage may be configured to dissipate MRI induced energy (due to RF and/or MR fields) from the supply voltage line. This MRI induced energy may be stronger and/or longer than energy caused by electrostatic discharge (ESD) from other devices, and these clamp stages described herein for dissipating MRI induced energy may be designed differently than other clamp stages intended to address induced energy from relatively short duration ESD. For example, ESD clamps typically only handle high but short duration (e.g., in the nanosecond (ns) range to tens of ns) currents due to an electrostatic discharge. In contrast, the MRI induced RF current bursts can last orders of magnitude longer (microseconds (μs) to milliseconds (ms) with potentially comparable current levels (e.g., sometimes up to and greater than one Ampere). Therefore, the MRI based clamps described herein are different than typical ESD protection circuitry.

The clamp may operate to dissipate this excess energy from the supply voltage line when the voltage and/or current on the supply voltage line reaches and/or exceeds a predetermined current threshold value and/or a predetermined voltage threshold value. In this manner, the clamp may operate to absorb excess energy from the supply voltage line only when necessary and otherwise be inactive to allow the system to operate with lower power requirements. In other words, the clamp may be activated to provide a low resistance that redirects excess current from other more sensitive electrical components and a high resistance when inactive to prevent load from being applied to the clamp when not needed. As described further herein, these one or more clamps, and other components, may operate to protect sensitive electrical components from excess current and/or voltage that may be induced from EMI, for example. Protection may be due to the clamps limiting the voltage and/or current on the supply lines of the integrated circuit from exceeding maximum allowable operating voltages or currents of the integrated circuit.

In the context of this specification, the term "coupled" can primarily be interpreted as "connected". However, the term "coupled" also includes configurations where another element, device, component and/or stage is connected in between two elements, devices, components and/or stage which are coupled to each other.

FIG. 1 is a conceptual drawing of an example neurostimulation system that delivers deep brain stimulation (DBS) according to the present disclosure. In other examples, neurostimulation system 100 may be directed to other applications such as spinal cord stimulation or pelvic floor stimulation. Neurostimulation system 100 comprises at least a controller 110 (e.g., a first module comprising one or more pulse generators or stimulation signal generators) that may be surgically implanted in the chest region 3 of a patient 1, typically below the clavicle or in the abdominal region of a patient 1. Controller 110 can be configured to supply the necessary current or voltage pulses (e.g., an electrical stimulation signal) to lead arrangement 130. Lead arrangement 130 may include one or more modules distinct from controller 110. DBS system 100 may further include a connecting cable 120 (e.g., an extension wire) connected to the controller 110 and running subcutaneously to the skull 2, such as along the neck 4, where it terminates in a connector. Controller 110 may also provide a power signal to lead arrangement 130 (which may include a second electrical module, e.g., an active lead can element) via connecting cable 120 or another connecting cable.

DBS lead arrangement 130 may be implanted in the brain tissue, e.g. through a burr-hole in the skull. DBS lead arrangement 130 may include one or more leads coupled to at least one module including a switch matrix (which may be housed within a second module). In addition, DBS system 100 may include one or more grounding electrodes in addition to electrodes carried in lead arrangement 130. Although system 100 is described for neurostimulation and/or neurorecording, system 100 may alternatively deliver different types of therapy (e.g., drug therapy or fluid delivery) or record different types of physiological characteristics (e.g., motion of patient, temperature, pressure, chemistry, etc.).

The neurostimulation and/or neurorecording system of system 100 may be a deep brain stimulation (DBS) system. Such a system may include a plurality of electrodes (e.g., greater than ten electrodes such as 20, 32, 40, 64 or 128 electrodes). To address or configure each of the electrodes, such as to set them active or inactive or reduce or increase the stimulation current provided by the electrode, control electronics may be provided in the second electronics module, for example, the active lead can element. These control electronics may include features such as a switch matrix to address each electrode of the plurality of electrodes and to distribute the stimulation current from controller 110 accordingly. Although only a single lead arrangement 130 is shown in FIG. 1, multiple lead arrangements may be coupled to controller 110 in other examples. Each lead arrangement may include a respective second electrical module and one or more respective leads coupled to the second electrical module.

The lead of system 130 may include at least 20 electrodes, e.g., approx. 30 to 45 electrodes, more specifically approximately 40 electrodes in one example or up to 128 electrodes in other examples. Each lead may include more than 128 electrodes in other examples. This number of electrodes may facilitate the creation of one or more stimulation fields selected to conform to a target region of tissue and which may form a three-dimensional field adapted to the target tissue or region. In this manner, only those tissue regions that are intended to be stimulated may be affected by the stimulation field provided by the plurality of electrodes.

In some examples, the electrodes may form a complex electrode array configured to create a stimulation field that is adapted to and conforms to the target region. The complex electrode array generally refers to an arrangement of electrodes at multiple non-planar or non-coaxial positions, in contrast to simple electrode array geometries in which the electrodes share a common plane or common axis (e.g., a plurality of ring electrodes stacked in one dimension). In this manner, electrodes of the complex electrode array may be disposed at different radial, circumferential, and/or axial positions of a lead.

An example of a simple electrode array geometry is an array of ring electrodes distributed at different axial positions along the length of the lead. An example of a complex electrode array geometry, in accordance with this disclosure, is an array of electrodes positioned at different axial positions along the length of the lead, as well as at different angular (or radial) positions about the circumference of the lead. These configurations may apply to cylindrically shaped leads and leads having other shapes such as triangles, squares, or other polygon or non-uniform shapes. In some examples, a lead may include a combination of one or more full ring electrodes extending around the full circumference of the lead along with one or more electrodes that do not extend all the way around the full circumference of the lead (e.g., one or more electrodes that form a complex electrode array).

Figure 2A:
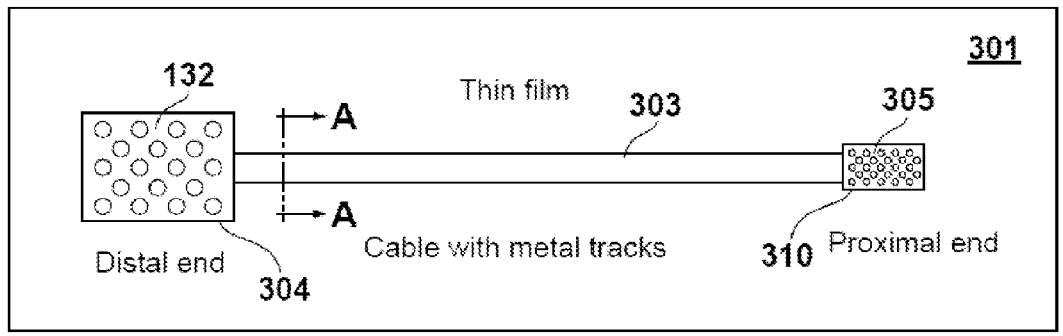
FIGS. 2A, 2B, and 2C are schematic diagrams of an example thin film, lead, and probe of a neurostimulation system for DBS.
Figure 2B:
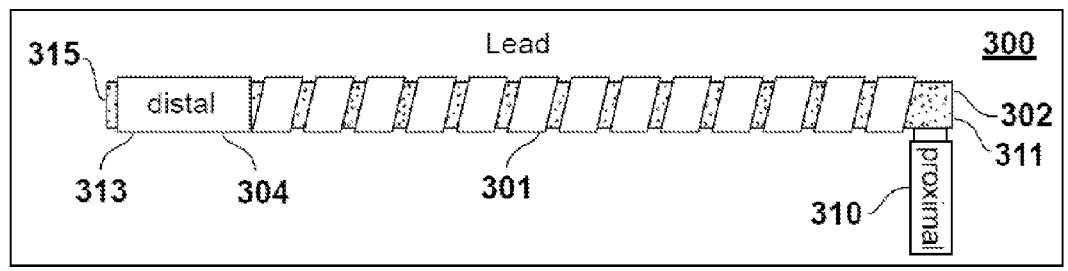
Figure 2C:
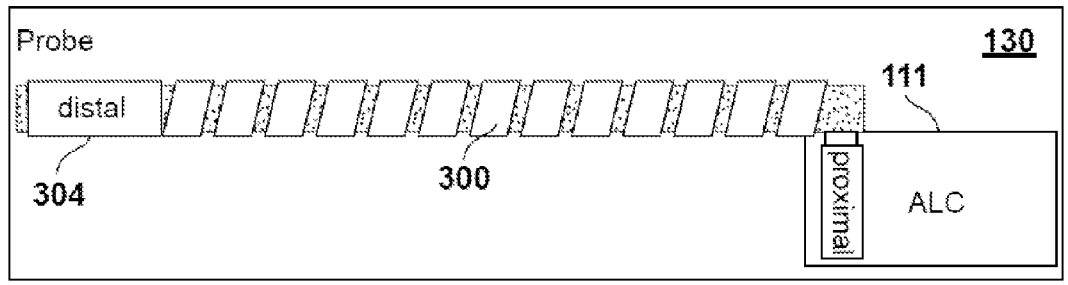

FIGS. 2A, 2B, and 2C are schematic diagrams of an example thin film, lead, and probe of a neurostimulation system for DBS. For example, FIG. 2A illustrates an example thin film 301, FIG. 2B illustrates an example DBS lead 300, and FIG. 2C illustrates an example Deep Brain Stimulation probe 130 that include DBS lead 300 and a second module 111 (e.g., an electrical module such as an active lead can). Second module 111 may include electronic means to address electrodes 132 (e.g., switch current or ground lines across each electrode) disposed on the distal end 304 of the thin film 301. Electrodes 132 may be arranged at the distal end 313 of lead 300 and next to the distal tip 315 of the DBS lead 300.

Lead 300 may include a carrier 302 for thin film 301. Carrier 302 may be sized and shaped to provide the mechanical configuration of DBS lead 300 and the thin film 301. In other words, thin film 301 may be wrapped around the circumference or diameter of carrier 302. Thin film 301 may include at least one electrically conductive layer and may be constructed of a biocompatible material. The thin film 301 may be assembled to carrier 302 and further processed to constitute lead 300.

The thin film 301 for a lead may be formed by a thin film product having a distal end 304, a cable 303 with metal tracks, and a proximal end 310. Proximal end 310 of the thin film 301 may be arranged at the proximal end 311 of lead 300 and is electrically connected to the second module 111. The second module 111 may include the switch matrix of the DBS steering electronics that selects configurations of electrodes 132. The distal end 304 comprises electrodes 132 for brain stimulation, for example. Proximal end 310 of thin film 301 includes interconnect contacts 305 for each metal track or line in the cable 303. The cable 303 comprises metal tracks or lines (not shown) to electrically connect each of distal electrodes 132 to a respective and designated proximal interconnect contact 305. In other examples, lead 300 may be constructed using other techniques and materials such as coiled conductors running the length of lead 300 to couple respective electrodes to module 111.

Second module 111 may include a switch matrix, or multiplexer, that is used to couple, or decouple, each electrode of electrodes 132 to one or more pulse generator lines and ground provided to second module 111 via a connecting cable (e.g. connecting cable 120 of FIG. 2). In other words, second module 111 may use the switch matrix to switch stimulation signal lines and a ground line across each of the electrodes 132. Second module 111 may also be electrically coupled to one or more ground electrodes (e.g., ground electrodes 320A or 320B of FIG. 4). In some examples, second module 111 may include other control electronics, such as a microprocessor or other integrated circuitry, resistors, and capacitors.

Figure 3:
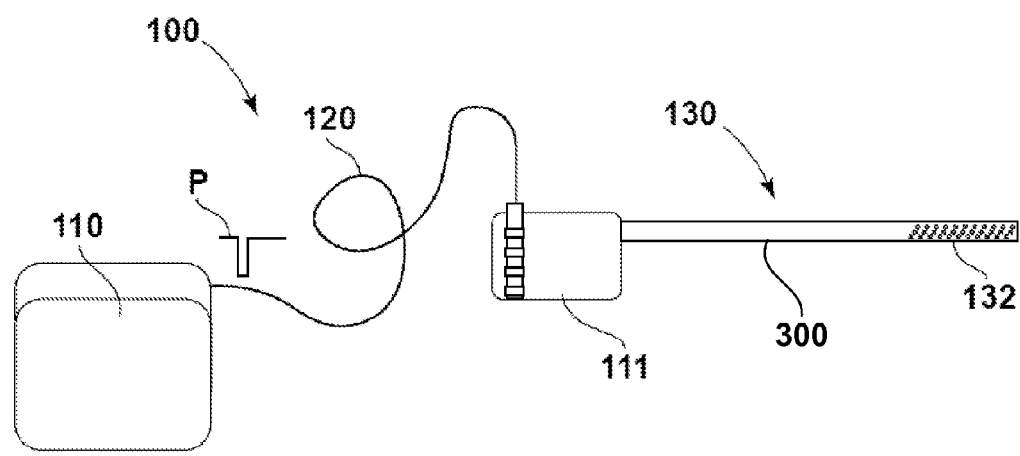
FIG. 3 is a conceptual drawing of an example system that delivers DBS.

FIG. 3 is a conceptual drawing of an example system that delivers DBS. System 100 is described for brain applications, such as neurostimulation and/or neurorecording as a deep brain stimulation system 100 as shown in FIG. 1. The probe system 100 may include at least one probe 130 (which includes lead 300 shown in FIGS. 2B, 2C, and 3) for brain applications with stimulation and/or recording electrodes 132. In one example, forty electrodes 132 can be provided on the outer body surface at the distal end of the probe 130. Controller 110 (e.g., a first module) may include one or more pulse generators that generator and supply pulses P or some other waveform to a second module 111 (e.g., an active lead can) by means of the connecting cable 120. In some examples, the controller 110 can be or include an implantable pulse generator. Controller 110 may include a power supply such as a battery and/or other components such as a telemetry module configured to communicate with external devices. In other examples, controller 110 may be configured to simultaneously couple to two or more different second modules 111 and respective probes 130 via one or more connecting cables 120. In other examples, system 100 may include additional distinct modules that provide additional functionality and/or additional modules that split the functionality provided by modules 110 and 111.

As described herein, system 100 may include first module 110, which includes one or more stimulation pulse generators and/or sensing circuitry. First module 100 may also include components such as a power supply, one or more processors, a memory, a communication unit for transmitting and/or receiving information from an external device, and other components. Second module 111 may include a switch matrix and, in some examples, one or more processors, a memory, and connectors for coupling lead 300 and connecting cable 120. In some cases, second module 111 may include a stimulation waveform generator that is provided in addition to, or instead of, a stimulation waveform generator (e.g., pulse generator) of module 110 to supply a stimulation signal to electrodes 132. Second module 111 may have a housing encompassing the control electronics such as the switch matrix. In some examples, the housing may be electrically nonconductive such as an epoxy or polymer that insulates and protects the components of second module 111. The electrically nonconductive material may reduce encapsulation of the housing and/or insulate the brain from any interference caused by the components of second module 111.

Connecting cable 120 may connect first module 110 to second module 111. The plurality of electrodes 132 are disposed distal of second module 111 and on lead 300 of probe 130. The control electronics for the plurality of electrodes 132, that may or may not include a grounding electrode for system 100, may provide at least one of neurostimulation and/or neurorecording via at least one electrode of the plurality of electrodes 132. The control electronics are arranged in at least the first module 110 and the second module 111, but one or more additional modules may also include at least some of the control electronics. As described in FIG. 2A, probe 130 may include lead 300 constructed of a thin film 301 carrying the plurality of electrodes 132. Lead 300 may be electrically coupled to the switch matrix of second module 111.

Figure 4:
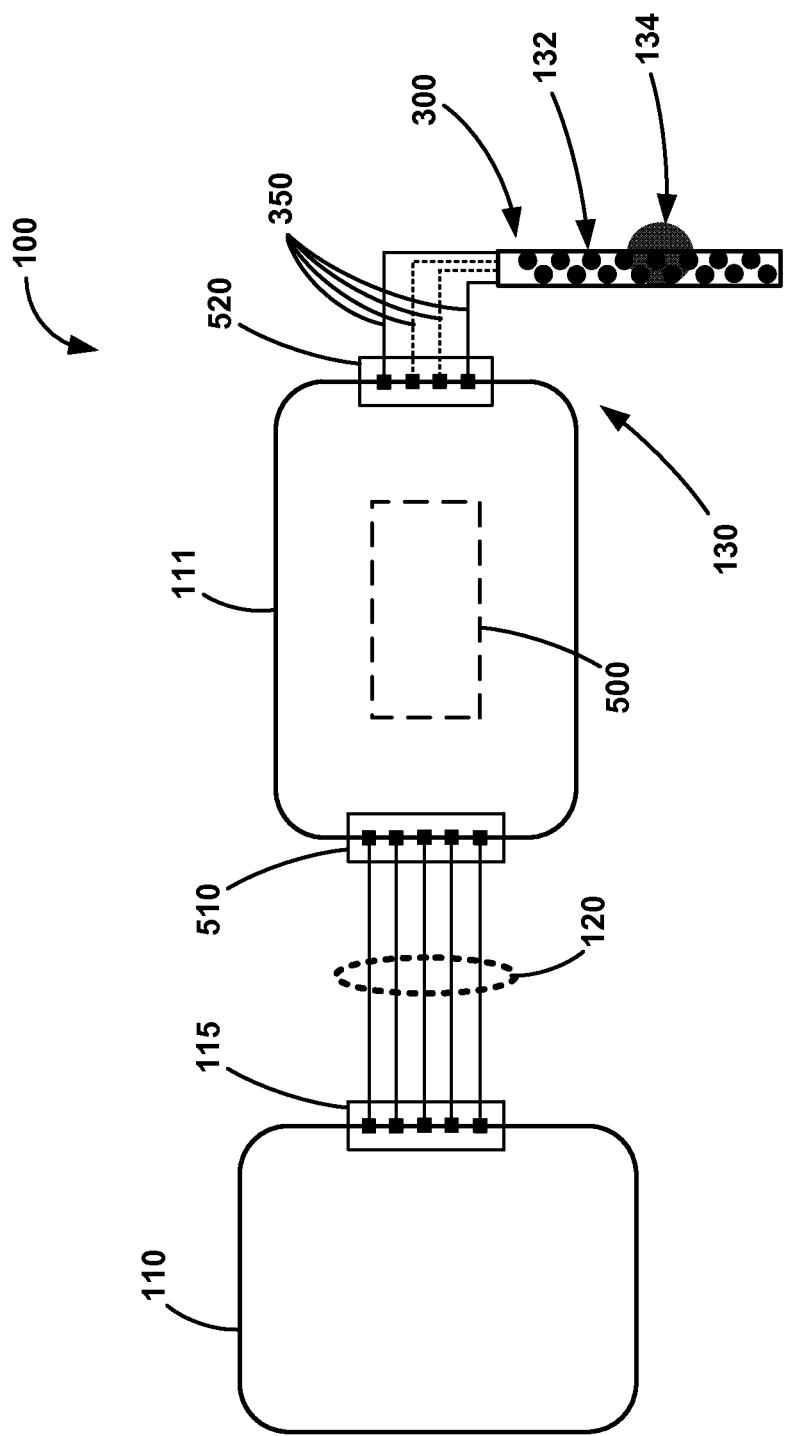
FIG. 4 is a schematic diagram of an example DBS system that includes a first module in communication with a second module coupled to a medical lead.

FIG. 4 is a schematic diagram of an example DBS system 100 that includes a first module 110 in communication with a second module 111 coupled to a medical lead 300. As shown in FIG. 4, second module 111 also includes electronic module 500 that is integrated into the housing of second module 111 (e.g., an active lead can). System 100 includes DBS probe 130 as discussed in FIGS. 2B and 3 and includes first module 110 (an implantable pulse generator) and second module 111. Second module 111 may include an array of electronic switches (e.g., a cross-point switch matrix) configured to selectively connect one or more of electrodes 132 arranged at the distal end of lead 300 with pulse generator lines of first module 110. In this manner, selected electrodes of electrodes 132 may be used to generate stimulation fields such as stimulation field 134. In addition, system 100 may be configured to record neural activity. First module 110 and second module 111 are connected through an interface cable 120 which may include one or more conductors that couple respective pairs of connections on first module 110 and second module 111. In the example of FIG. 4, interface cable 120 includes five distinct conductor lines. Accordingly, first module 110 includes a 5-pin low-count feedthrough (LCFX) connector 115 which is connected via the interface cable 120 with the 5-pin LCFX connector 510 of second module 111.

In the example of FIG. 4, second module 111 includes a multi-pin connector with a S-pin LCFX connector 510 for the interface cable 120 and a 40-pin high-count feedthrough (HCFX) connector 520 for lead 300. Each electrode of electrodes 132 is connected to second module 111 via a respective pin of connector 520. In some examples, the two feed-through connectors 510 and 520 may be constructed with a high pin density to reduce the area of second module 111 devoted to the connectors. However, this reduction in area advantage may be possible if the electrical components of second module 111 can be reduced in size in similar proportions as the feed-through connectors 510 and 520. Moreover, a very thin second module 111 may provide a benefit of reducing the module's impact on skin erosion, but such small thicknesses may include a reduction in height of both feedthrough pins 511 and 521 (shown in FIG. 5) in addition to the high pin density and a reduction in the height of both and interior electrical components. In this manner, both the electronics volume and area of second module 111 can be miniaturized to realize a small second module 111 for implantation in, on, or near the cranium of a patient.

Although these features related to connectors 510 and 520 and feedthrough pins 511 and 521 are discussed in relation to second module 111, these techniques to shrink the size of second module 111 can also advantageously be applied to first module 110, or any other implant module of system 100. In some examples, these reductions to module size may also reduce certain functionalities and/or battery capacity.

As discussed further below in FIGS. 7, 8, and 9, electronic module 500 may include one or more clamp stages configured to protect other electrical components within second module 111 from excess energy caused by EMI induced currents and/or voltages. For example, a clamp stage may include at least one energy dissipating element, such as a variable resistor or transistor. In particular, a transistor can be configured to have a variable resistance in response to a control signal (e.g., at the control input of the gate or base of the transistor). In this manner, a transistor can be considered a variable resistor in the context of this specification. In some examples, the clamp stage may be configured as a shunt stage or more specifically as a shunt regulator that draws excess current away from other electrical components (e.g., components of an integrated circuit).

Although it is possible to integrate some EMI filtering in small implants such as second module 111, EMI filtering may not be sufficient to protect the electronics of second module 111 against the strong interference of, for example an MRI machine. According to the aspects and embodiments described herein, protection circuitry can be integrated by way of special (e.g., on-chip) clamp stages on all relevant supply domains of the impacted electronics to cope with the MRI induced excess current and overvoltage stress. These clamps may absorb the excess energy or otherwise direct the excess energy away from more vulnerable or sensitive electrical components such as various portions of the integrated circuit.

In addition, one or more integrated circuit of electronic module 500 can further include an electrostatic discharge (ESD) protection circuitry. The ESD protection circuitry can be coupled between the clamp stage and a bond pad which is coupled to the at least one connector of the integrated circuit. The ESD protection circuitry can include a diode that is arranged between the bond pad and the supply voltage line. In some examples, the diode is reversely biased during normal operation of second module 111. This means that the anode of the diode is coupled to the negative potential and the cathode of the diode is coupled to the positive potential during normal operation. This reversely biased configuration of the diode not only provides ESD protection to the bond pad but may also advantageously prevent the clamp stage from contributing, or adding, to the load on the bond pad in normal operation.

In one potentially advantageous aspect, the integrated circuit of electronic module 500 may include two types of clamp stages, with both types of clamp stages being coupled between a supply line and ground. Each type of clamp stage may advantageously be coupled to a respective supply line of a different supply voltage domain such that each type of clamp stage may be configured for the types of voltages typically on each supply line. Accordingly, an integrated circuit can include a first clamp stage type and a second clamp stage type different than the first clamp stage type. In other words, the first clamp stage type can be configured to be coupled to a supply line of a first supply voltage domain and the second clamp stage type can be configured to be coupled to a supply line of a second supply voltage domain. Each of the supply voltage domains may usually provide different voltages and/or current during normal operating conditions.

The first and the second supply voltage domains can be different supply voltage domains having different supply voltage levels. Otherwise, the same type of clamp stage may be used for different supply voltage domains. In other words, a magnitude of a supply voltage level of the first supply voltage domain can be greater with respect to system ground than a magnitude of a supply voltage level of the second supply voltage domain with respect to system ground. In this manner, an advantage of including different clamp stages for different supply voltage domains has the advantage that the clamp stages can be configured differently such as utilizing different areas on the integrated circuit and taking account of the different EMI situations on the supply voltage lines.

In another aspect, the different clamp stages of the first type and/or second type can be configured to be switched between a first state and second state. In the first state, the respective clamp stage (or the energy dissipating element of the clamp stage) is not operable to dissipate energy. The first state may be used during a normal operating mode of second module 111 to prevent the clamp from adding to the resistive load of the circuitry. In the second state, the clamp stage (or the energy dissipating element in the clamp stage) is operable to dissipate energy if the voltage and/or current on the supply line of the first supply voltage domain reaches and/or exceeds a threshold value. In other words, the clamp stages can be switched on and off (e.g., first module 110 and/or second module 111 may provide a control signal that switches the clamp stage between the first and second states) or automatically switch on or off (e.g., the control signal that switches each clamp stage on or off may be generated by a change in operational voltage associated with normal operation or a system off state).

The first clamp stage type may include one or more high voltage metal-oxide-semiconductor field-effect transistor (MOSFET) transistors. These types of transistors may allow the first clamp stage type to cope with comparatively high voltage levels. The second clamp stage type may then be configured for lower voltage levels as compared to the first claim stage type. The first clamp stage type may also be configured to be switched on and off by a control signal. FIG. 8 describes an example of the first clamp stage type.

In one example, the second clamp stage type can include an operational transconductance amplifier (OTA) having at least a first input, a second input, and an output. The second clamp stage type may also include a reference signal source (for example a bandgap circuit source) for providing a threshold signal for the first input of the OTA and a transistor coupled to the output of the OTA. The second input of the OTA can be coupled to the supply line and the output of the OTA can be coupled to a base or gate of the transistor. Accordingly, the OTA can switch the transistor on when the voltage level (or current level) of the supply line reaches and/or exceeds the reference voltage level (or current level) and switch the transistor off when the voltage level of the supply line remains below the reference voltage level (or the threshold signal provided by the reference signal source). Although the transistor coupled to the output of the OTA is generally described as being coupled between a supply line and ground, the transistor may be coupled between two supply rails having differing voltages or currents in other examples. In some examples, the clamp stage having an OTA may not be able to handle ESD because it may not be fast enough to dissipate the energy from an ESD. This second clamp stage type is further described in the example of FIG. 9.

In addition to inclusion of one or more clamps, second module 111 may include additional changes for various components to accommodate the absorption of excess current provided by the clamps. For example, the dimensions of the bond pad and/or other interconnections like wires between the bond pad and the respective clamp stage may be enlarged to accommodate larger currents associated with EMI induced energy. In other words, these connections and components that may be coupled to the clamps may be configured differently than other connections between other lower voltage and/or lower current portions of electronic module 500.

In one example, electronics module 500 (and second module 111) may include at least one connector, at least one integrated circuit (e.g., an application specific integrated circuit (ASIC)), at least one DC blocking element between the connector and the integrated circuit, and at least one connection to system ground. Electronics module 500 may include at least one variable resistor between the DC blocking element and the connection to system ground. The variable resistor may be configured to dissipate RF induced current due to EMI. The EMI can be caused by an MRI machine emitting magnetic fields of a field strength between 0.2 Tesla up to more than 10 Tesla, or more typically 1 Tesla to 3 Tesla. The variable resistors may form or form part of a clamp stage. The clamp stage may be located in the integrated circuit, i.e. on the same chip or on the substrate together with the integrated circuit.

An electronics module (e.g., first module 110 and second module 111) may be particularly advantageous in a system for neurostimulation and/or neurorecording, although it is contemplated that the electronic modules of this disclosure is not necessarily limited to such systems. The EMI induced in an electronics module is mainly received through lines connected to the electronics module or more specifically through lines connected to connectors of the housing of the electronics module (e.g., the housing of second module 111 that constitutes or includes the electronics module). The aspects and embodiments of the present disclosure may advantageously apply to all signal lines which are vulnerable to high EMI (such as EMI induced by MRI systems), the respective connectors (bond pads) and all supply voltage domains of the electronic module.

Other components and aspects of an electronics module and the system for neurostimulation are described in the following as these components may advantageously cooperate with the advantageous aspects of the electronics module. For example, a medical lead 300 may include at least one thin film, where the thin film includes a proximal end and a distal end. Lead 300 may further include a plurality of electrodes carried on the distal end of the thin film. The thin film may include at least one electrically conductive layer, preferably made of a biocompatible material. The thin film may be assembled to the carrier and further processed to constitute the lead element. The thin film for lead 300 is preferably formed by a thin film product having a distal end, a cable with metal tracks and a proximal end.

The distal end of lead 300 may be the end of the lead that is configured to be implanted adjacent body tissues. In particular, in case of a lead for brain application, the distal end of the lead is the lower end of the lead, which is deep of the burr-hole of the skull, through which lead 300 is implanted.

Second module 111 may include electronic means to address (e.g., receive electrical signals from and/or transmit electrical signals to) the plurality of electrodes 132 and at least one connector (e.g., connector 520) on second module 111 to connect electrodes 132 to second module 111. Lead 300 may include respective metal tracks or conductors 350 for each electrode of electrodes 132. Further, second module 111 may be hermetically sealed or substantially hermetically sealed and may include electronic components to address the plurality of electrodes 132 at the distal end of the thin film. In some examples, second module 111 may include a switch matrix configured to selectively address each electrode. The plurality of electrodes 132 may include 5-10 or more electrodes, e.g. 16 or 32 electrodes, or in other embodiments e.g. 40 electrodes or more, e.g. 128 electrodes. The electrodes 132 may be arranged such that the electrodes are evenly distributed or arranged over the distal end of lead 300. Alternatively, electrodes 132 may be arranged in an uneven manner to provide a predetermined pattern or two or more areas with higher electrode density.

In one example, second module 111 may include a multi-pin connector (e.g., connector 510) such as a LCFX connector with five pins for the interface cable 120 between second module 111 and first module 110. Second module 111 may also include a HCFX connector (e.g., connector 520) with 40 pins for lead 300, for example. However, connector 520 may have different numbers of pins or the pins may be distributed between two or more connectors similar to connector 520. Any other suitable number of pins for the LCFX and HCFX may be also used if needed. First module 110 may include similar connectors in other examples.

Furthermore, it is possible that electronic module 500 may include at least one filtering element such as a feed-through filter (e.g., feed-through filter 567 of FIG. 6) and/or at least one blocking element. The feed-through filter and blocking element may be disposed between the feed-through pins of electronic module 500 and an integrated circuit such as integrated circuit 600). The blocking element may be a DC blocking element (e.g., DC blocking element 568 of FIG. 6) in some examples. In some examples, an integrated passive device may include at least one filtering element. The filtering element may be, for example, a feed-through filter and/or the at least one blocking element such as a DC blocking element.

In one example, the filtering element may be configured in a first integrated passive device and the blocking element is realized in a second integrated passive device, where such passive devices may be respective layers of electronic module 500. For example, the filtering element and/or the blocking element and/or the integrated circuit (e.g., an ASIC) may be stacked one upon the other within electronic module 500. The stack may be configured as a thin stack with a low volume. The filtering can be provided by any means which is/are configured to provide filtering of electrical signals such as EMI currents and/or voltages. In particular, a filtering can be provided by any passive circuitry or passive network.

The filtering element may be configured such that interferences, in particular unwanted interferences caused by mobile phones or the like, can be removed before the interferences may enter the housing of the system. Therefore, the filtering element may provide protection against electromagnetic interference (EMI) (e.g., interference from mobile phone induced fields while the patient is using its mobile phone). The filtering element may be or may include an RF feed-through filter in some examples. The filter may include components such as a capacitor, a coil, an inductor, a resistor, and/or any other suitable passive component. It should be noted that the size, area, and/or volume of the filtering elements may not be increased arbitrarily to cope with stronger EMI as the size of second module 111 or electronics module 500 are desired to be as small as possible.

As described herein, clamp stages may remove higher or stronger voltages and/or currents on respective supply lines of the integrated circuit that may occur due to EMI, such as EMI caused by an MRI machine. At least one clamp stage of a first type of clamp stage may be used for higher voltages and may be switched off during normal operation, i.e. during neurostimulation or neurorecording. If the patient undergoes an MRI scan, system 100 may turn off other parts of the integrated circuit (e.g., an ASIC) of second module 111, except for the first and/or second clamp stage types. With the clamp stages being active, the clamp stages may be configured to dissipate EMI induced energy from the respective supply lines and thereby prevent damage to electronic components and circuits of the integrated circuit that may otherwise occur.

The one or more blocking element may be configured to prevent leakage current, such as DC leakage current flow. Since it may be desirable to reduce or eliminate DC current flow through the patient having an implant such as a deep brain stimulator, the blocking element may reduce or eliminate any DC current flow even if a failure occurs in the implant's electronics. In one example, DC leakage is prevented by the application of DC blocking capacitors in second module 111. With a high number of feed-through pins, integration of these DC blocking capacitors into a substrate that can be stacked with other components into second module 111 or electronic module 500 may help to achieve a minimum volume and area of the module as opposed to the application of discrete components. In other words, the DC blocking capacitors may be integrated into a substrate to which an integrated circuit is attached.

As discussed herein, electronic module 500 may include one or more integrated circuits. For example, an integrated circuit may be an ASIC that includes a part or all active electronics with some external passive electronics. For example, passive electronics may include one or more power supply decoupling capacitors. A substrate with integrated passive components (e.g., resistors, capacitors, and/or inductors) may be used as a substrate for off-chip (rerouting to) the ASIC. Together, the integrated passive components and one or more ASIC may be referred to as a hybrid or hybrid integrated circuit. System 100 may be constructed of a smaller size by incorporating one or more ASICs as the active electronic components for at least a part of system 100.

The integrated circuit including one or more clamps may provide for EMI protection while also reducing the volume needed to house all of these electrical components. Certain passive electronics that typically claim a large portion of the volume of an electronic module can be selected for integration into a substrate containing other circuitry or for other circuity to attach to in order to reduce the volume of the implanted system or module. Some of these passive components typically take up a larger portion of volume in the device because, for example, it is technologically not feasible to integrate inductors or capacitors with large values on an integrated circuit chip, it is too costly to include hundreds of nano-farad DC blocking capacitors and the capacitors consume too much chip area, and/or it is functionally undesired or ineffective to put the passive electronics on the ASIC die (e.g., feed-through filters are only effective when put close to and/or integrated with the feed-through pins and DC blocking capacitors should generally be electrically isolated from active electronics by integration on a separate die and/or substrate). The volume and area claim of the passive components can be particularly high if feedthrough connectors have a high pin density thus requiring feed-through filter networks. However, by combining integrated passive devices and one or more ASICs, the entire electronics package can be reduced in size.

Moreover, the integrated passive device may include or be connected to one or more sections of interconnects (e.g., one or more low-count feed-through pin connections, one or more high-count feed-through pin connections, one or more ASIC, one or more integrated passive device, and/or at least one bias terminal). In one example, an input and/or output of the integrated passive device may be connected to the filtered output and/or input via at least one capacitor, at least one resistor, and/or at least one inductor. In addition, or in an alternative, the integrated passive device may include a substrate and/or at least one diode and at least one passive electronic component which is arranged on and/or in the substrate. At least one filtering element may then filter the signals received by and/or transmitted through the respective feedthrough pins.

The housing of second module 111 may be configured as a miniaturized Faraday cage. In one example, the housing may be configured with an overall thickness of less than approximately 10 mm, less than approximately 5 mm, less than approximately 4 mm, or less than approximately 3 mm.

In one example, the dimension of the housing of second module 11 can be less than approximately 20 mm in length and less than approximately 10 mm in width. These dimensions may provide for a volume of second module 111 that is sufficient for implanting at or near the cranium of the patient or at any other location. The techniques described here with respect to second module 111 or any other component may be used to manufacture other modules with relatively low volumes but arranged to provide different dimensions. For example, although a very thin housing may be advantageous for DBS applications, a housing having a greater thickness with less length and less width may be advantageous for implantations at other locations in the body.

Figure 5:
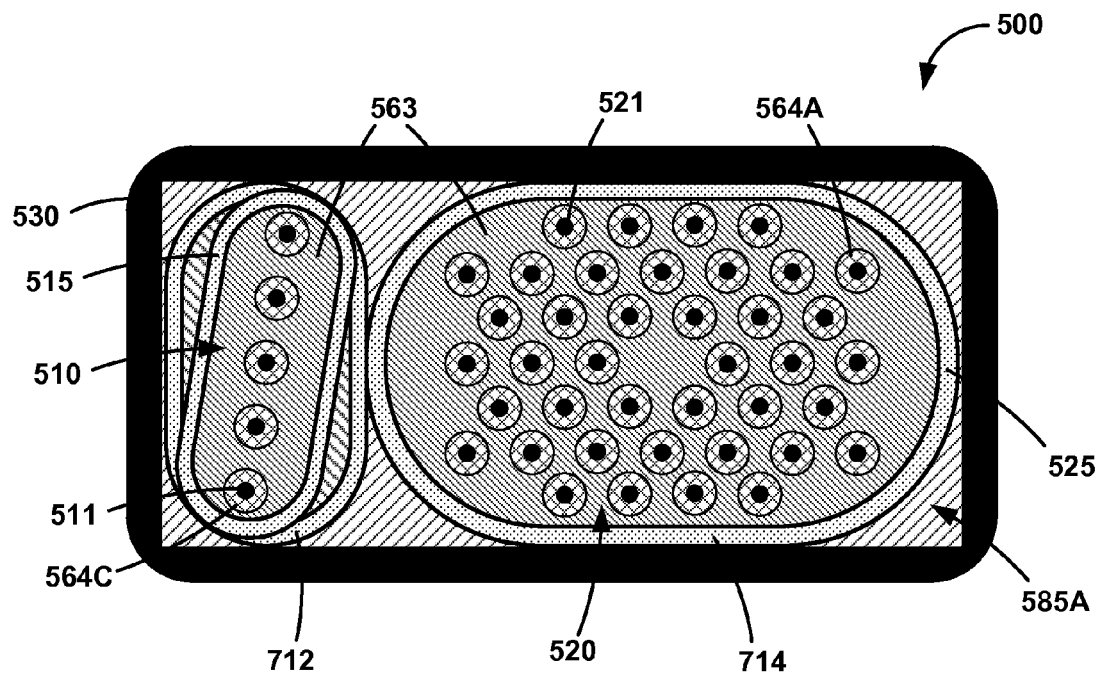
FIG. 5 is a schematic drawing of a top view of an example electronic module showing a top feedthrough and an underlying feedthrough capacitor of an integrated passive device.
Figure 6:
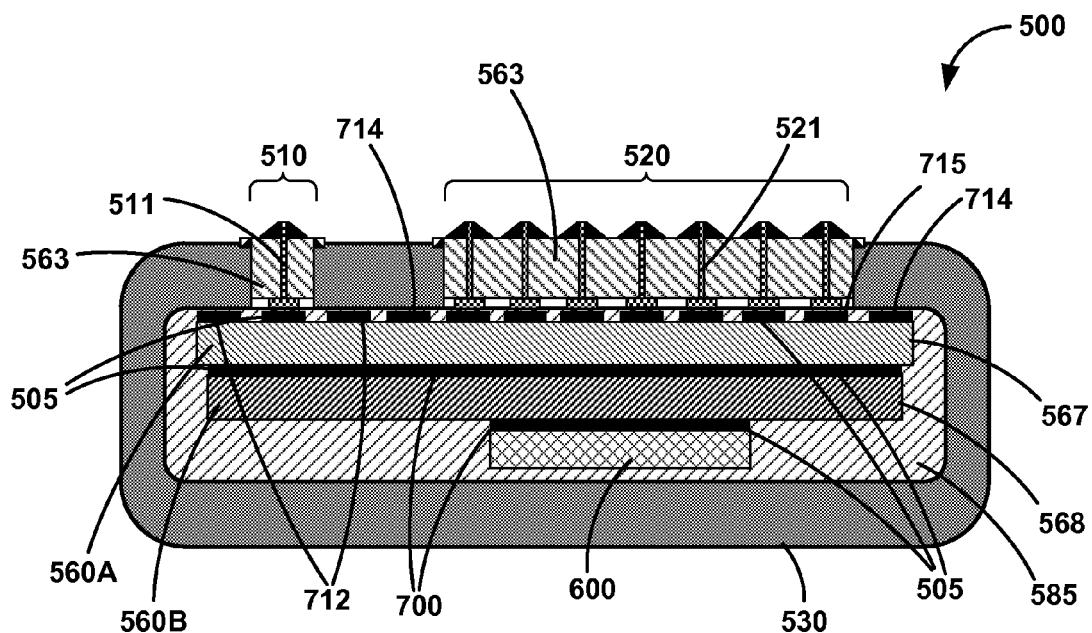
FIG. 6 is a schematic cross-sectional view of the example electronic module of FIG. 5.

Additionally, electronic module 500 may include at least one first connector element, e.g., the LCFX connector of connector 510 of FIGS. 5 and 6, and at least one second connector element, e.g., the HCFX connector of connector 520 of FIGS. 5 and 6, and may be configured such that electronic module 500 is directly and/or indirectly connectable or connected to a controller (e.g., first module 110) via an integrated passive device. The first module 110 may be configured to provide various functions. For example, first module 110 may be configured to supply, provide, and/or measure at least one voltage, at least one current, at least one voltage waveform, and/or at least one current waveform. First module 110 may transmit and/or receive such electrical signals via separate or combined lines. In one example, first module 110 may be connected to second module 111 via one or more stimulation lines, a recording line, a clock line, a power line, and/or a communication line. Each of these lines may be physically separate from each other. Alternatively, two or more functionalities (e.g., different signals used to provide different information and/or power) may be multiplexed or otherwise combined onto a single physical line. The second connector element (e.g., connector 520) may be configured to couple electronic module 500 directly and/or indirectly to one or more medical leads (e.g., lead 300) for neural stimulation and/or recording. In some examples, electronic module 500 may be described as including the electrical components of second module 111 without any additional electrical components other than electronic module 500.

Electronic module 500 and/or its components advantageously increase the likelihood that any electromagnetic interference (EMI) is kept outside of or away from electrical components of second module 111 that may be vulnerable to EMI. In addition, electronic module 500 may include one or more components that prevent EMI generated inside second module 111 from radiating outside of module 111. A conductive (e.g. titanium) housing may provide electromagnetic shielding with the electromagnetic opening formed by the (non-conductive) ceramic with the embedded LCFX and HCFX pins being electromagnetically closed by the feed-through filtering element of electronic module 500. This filtering element, such as an array of feed-through capacitors, may be configured to redirect any EMI induced currents to the (conductive) housing of second module 111. In this regard, it should be noted that the relatively small size of the second module 111 may prevent complete suppression of extremely strong EMI induced currents such as those currents due to MRI with only the use of a filtering element. Therefore, as described herein, an integrated circuit may include one or more clamp stages on respective supply voltage lines of all supply voltages domains. Through the incorporation of the EMI suppression components described herein, such as one or more clamp stages (e.g., MRI clamp stages), EMI filtering capacitors, ESD protection circuitry, DC blocking capacitors, conductive housing, feedthrough pins, etc.), second module 111 may be configured to sufficiently suppress extremely high EMI induced voltages and/or currents and prevent electrical components (e.g., integrated semiconductors components) from being damaged or otherwise adversely affected by EMI.

As described herein, the integrated passive device may include one or more passive electronic components, such as at least one capacitor, at least one inductor, one or more diode, and/or at least one substrate terminal. Any combination of these components may be used to passively limit any induced current and/or voltage caused by EMI from affecting more sensitive electrical components.

In some examples, the integrated passive device may include one or more feed-through capacitors that are mounted on and/or integrated into a substrate. In one example, the integrated passive device may include a ceramic substrate and/or one or more integrated DC blocking capacitors mounted on and/or integrated into a substrate (e.g., a silicon substrate). Some examples, may include an integrated passive component manufactured from one or more of the following: a flexible organic capacitor in a flex foil and/or printed circuit board (PCB), a (screen) printed capacitor on a ceramic substrate, a capacitor built using thick film on ceramic technology, a capacitor that is built on a ceramic substrate using physical vapor deposition (PVD), a stack of ceramic substrates with a (screen) printed thick film capacitor (e.g., a capacitor built using low temperature co-fired ceramic (LTCC) technology), or a 3D-in-silicon capacitor. In some examples, the integrated passive component may be manufactured from a metal-insulator-metal (MIM) capacitor on silicon technology.

The feed-through filter described herein may include one or more filtering elements such as one or more feed-through capacitors. In one example, the feed-through capacitors may be (screen) printed on the top side of the substrate of the integrated passive device. In some examples, the feed-through capacitors may be made of a sandwich of two or more conductive layers with a relatively high-k dielectric in between. The one or more integrated DC blocking capacitors may be incorporated as a part of the at least one blocking element in some examples.

In some examples, the substrate may include a contact surface portion, such as a ground plane on the substrate top which is directly and/or indirectly electrically (e.g. galvanically, ohmically, and/or capacitively) connected to a conductive housing of the electronic module. In some examples, a ring of conductive adhesive (e.g., conductive adhesive epoxy) may be incorporated such that the feed-through capacitors and the housing together form a high-frequency closed and miniaturized Faraday cage. The Faraday cage may then only be penetrated by a substrate with feedthrough pins that are capacitively and/or electrically (e.g., galvanically) coupled to the Faraday cage.

The housing of second module 111 may be a conductive housing, such as a titanium housing in one example. A metal housing may combine mechanical protection of the housing in addition to electromagnetic shielding. Alternatively, a metalized polymer can be used for mechanical protection and electromagnetic shielding within second module 111.

These passive and active EMI protection elements may keep out most if not all electromagnetic interference (EMI) from the area of second module 111 that is vulnerable to EMI (e.g., one or more integrated circuits). In addition, these passive and active EMI protection elements may prevent EMI generated inside second module 111 from radiating to other components of the system outside of second module 111. Each feed-through pin of second module 111 may connect to the top contact (e.g., a gold top contact) of a single capacitor in an array of feed-through capacitors (e.g. a thick film capacitor array) via stud bumps. Through-hole signal vias may connect the feed-through pins to one or more interconnect layers on the bottom side of the substrate. Each metal layer can have a maximum area fill factor so that a maximum overlap between all metal layers is achieved, the capacitance per printed dielectric layer is increased, and a high-frequency closed Faraday cage with the conductive housing of the module can be formed.

A minimum spacing between the individual top contacts and a minimum spacing between the through-hole vias and the ground plane may increase the filter's efficacy because it may increase the capacitance per pin and minimize the size of the openings in the metal layers. In some examples, an additional ground layer can be applied to electrically close or substantially close the filter's 3D structure. In some examples, the mutual ground plane of all array capacitors may extend beyond the capacitor arrays itself and may be connected with a ring of ground vias to the other side of the substrate to provide ground to the interior of second module 111. Alternatively, or additionally, the top and bottom substrate ground planes can be connected via metallization wrapped around the substrate's side edges. In this manner, the ground plane on the substrate top may be electrically connected to a conductive housing of second module 111 via a ring of conductive adhesive such as a conductive adhesive epoxy. The conductive adhesive may allow the feed-through capacitors and the housing together to form a high-frequency closed and miniaturized Faraday cage only penetrated by the through-hole substrate vias. In other words, EMI currents may be diverted through feed-through capacitors to the conductive housing before the EMI currents can enter the housing of second module 111. In addition, embedding of the feed-through filter in the conductive housing may prevent or at least reduce any EMI generated inside second module 111 from radiating outside of second module 111.

As described herein, second module 111 may also include a multi-layer structure (e.g., wherein the filtering element forms a first layer, the blocking element forms a second layer, and the integrated circuit such as an ASIC forms a third layer). This multi-layer structure may provide an advantage in that all or almost all electronic components fit within a very small volume and area particularly useful for implantable medical devices.

Moreover, second module 111 may include a dedicated routing substrate and/or an already available substrate. The substrate may provide routing for passive components and/or active components mounted outside an integrated passive device. For example, at least one discrete component, e.g., a surface mounted device (SMD), may be attached to the substrate. The routing substrate may be the substrate that also carries DC blocking elements, e.g., DC blocking capacitors.

Efficient filtering of electrical signals, such as filtering for improved EMI suppression, can be realized with a combination of passive components, capacitors, resistors, and inductors. For an integrated passive device, the feed-through filtering element may include at least one resistor (e.g., a series resistor), an inductor (e.g., a series inductor), and a capacitor (e.g., a parallel capacitor). The resistor, the inductor, and/or the capacitor may be configured such that a parasitic filter resonance may be dampened and/or the filter's suppression (e.g., the suppression of electromagnetic interference) may be improved and/or increased. In this manner, a series resistor, an inductor, and/or a capacitor can be added to dampen any parasitic filter resonances and/or to increase the series impedance of the filtering element towards the connected electronics. These components may thus improve the high-frequency shorting efficacy of the filtering element to the housing of second module 111.

These passive EMI protection features may be used in addition to active EMI protection components such as the one or more clamp stages described herein. Therefore, the one or more clamp stages also contribute to the suppression of EMI induced currents caused by strong magnetic and/or electric fields like those due to MRI.

Although various active EMI protective elements and passive EMI protective elements have been described with respect to second module 111, these same EMI protective elements may be provided in other modules of the system. For example, first module 110 may include one or more clamp stages to absorb any induced currents and/or voltages from EMI. In addition, or alternatively, one or more passive EMI protection components such as a feed-through filter and/or blocking capacitors may be included within first module 110.

FIG. 5 is a schematic drawing of a top cross-sectional view of an example electronic module 500 showing a top feedthrough and an underlying feedthrough capacitor of an integrated passive device for second module 111. FIG. 6 is a schematic cross-sectional view of the example electronic module 500 of FIG. 5. As shown in FIGS. 5 and 6, both the LCFX connector 510 and the HCFX connector 520 are on the outside of electronic module 500 as well as on the top of the substrate of the capacitor array (e.g., DC blocking capacitors 568 of FIG. 6) on the inside of electronic module 500. DC blocking capacitors 568 are thus underneath the feedthroughs of connectors 510 and 520, as shown in FIG. 6. Ground plane 585 (FIG. 6) of the capacitor array is electrically connected via the top part 585A of the ground plane 585 to the housing 530 of the second module 111 via a rings of conductive adhesive 712 and 714 (e.g., an epoxy glue), shown in FIG. 5.

A ground ring of the LCFX connector 510 can be directly and/or indirectly electrically (galvanically and/or ohmically) connected to the housing 530 of second module 111 via a ring of conductive adhesive 712 (e.g., epoxy glue). A ground ring of the HCFX connector 520 can be directly and/or indirectly electrically (galvanically and/or ohmically) connected to the housing 530 of second module 111 via a ring of conductive adhesive 714 (e.g., epoxy glue). In some examples, a single ring of conductive epoxy glue may be used to surround both LCFX and HCFX connectors 510 and 520, respectively, to electrically connect the housing 530 to the top part 585A of ground plane 585. The spacing and/or pattern of each of connectors 510 and 520 may be different in other examples. For example, feed through pins of connector 510 may be configured in a line, arc, or other geometric shape. In another example, the feed through pins of connector 520 may be in a staggered configuration of FIG. 5 or aligned in rows, rings, or any other pattern. In other examples, multiple feedthroughs may be combined together such that fewer feed through pins are provided or all connections could be combined into a single feed through in some examples.

Electronic module 500 includes HCFX connection pins 521 (within connector 520) and LCFX connection pins 511 (within connector 510). HCFX connection pins 521 are connected to DC blocking capacitors 568 of integrated passive device 560B (FIG. 6) and also to the feed-through filter capacitors 567 of integrated passive device 560A. Integrated passive devices 560A and 560B may be referred to, collectively, as integrated passive devices 560. Although not explicitly shown, the LCFX connection pins 511 are also connected to integrated passive devices 560 to realize the same DC blocking and EMI filtering for the LCFX connector 510 as the HCFX connector 520.

Each feed-through pin of connection pins 511 and 521 contacts a top contact of a capacitor (e.g., a gold top contact) on the substrate top of thick film integrated passive device 560A. The HCFX connection pins 521 are contacted to respective capacitors 564A and the LCFX connection pins 511 are contacted to respective capacitors 564C. The top contacts are also the top plates of capacitors 564A and capacitors 564C. In this manner, a thick film substrate with screen printed capacitors 564A and capacitors 564C may form a single feed-through filter substrate 567 (FIG. 6) that is directly put on top of and connected with feedthrough connection pins 511 and 521.

The LCFX connector 510 may include a titanium flange 515 forming a border around the LCFX connector 510. Similarly, the HCFX connector 520 may include a titanium flange 525 forming a border around the HCFX connector 520. The titanium flanges 515 and 525 may be integrated in the housing 530 of second module 111. Insulator 563 may be configured to electrically insulate capacitors 564A and 564C. In some examples, insulator 563 may be formed of ceramic.

As shown in FIG. 6, electronic module 500 includes a filtering element such as feed-through filter 567, a blocking element such as DC blocking element 568, and an ASIC 600 (or any other one or more integrated circuit). In some examples, integrated passive devices 560 include feed-through filter 567 and DC blocking element 568.

The filtering element may be provided, in some examples, by any circuitry or electrical components configured to provide filtering to electrical signals. In some examples, a passive network of electrical components may provide the filtering for electrical signals passing through the feedthrough pins 521 and 511. In some examples, the filtering element (e.g., feed-through filter 567) may be configured such that interferences, such as unwanted electrical interferences caused by mobile phones or other communications devices, can be removed before the interferences enter a part of the housing for the electronics of second module 111. In this manner, the filter can advantageously provide protection of the interior electronics against electromagnetic interference (EMI) induced currents and/or voltages that could be caused by mobile phone induced fields while the patient is using a mobile phone. Conversely, the filtering components may also limit or prevent high-frequency interference generated inside second module 111 from to radiating outside of second module 111 such as being transferred to another electrical module or electrodes carried by a medical lead.

In some examples, the filtering element (e.g., feed-through filter 567) may be or may include an RF feed-through filter. The filter may include one or more capacitors, coils, inductors, resistors, and/or any other suitable passive electrical component. The blocking element (e.g., DC blocking element 568) may be configured such that in the event of a leakage current, (e.g., DC leakage current), the DC current flow is prevented or reduced from being transferred past the filter element. DC current flows are typically avoided in a patient (e.g., a person carrying a deep brain stimulator), and even a single failure of the implant's electronics may not be acceptable for the patient. DC current leakage may be prevented by including DC blocking capacitors of the DC blocking element 568. With a high number of feed-through connection pins 511 and 521 the DC blocking capacitors may be integrated to achieve a smaller volume and smaller area as opposed to inclusion of discrete capacitors for each feed-through connection pin.

ASIC 600 may include some or all of the active electronics and/or some external passive electronics, such as a power supply and decoupling capacitors. A substrate with integrated passive devices, shown in the example of FIG. 6 as the integrated passive devices 560A and 560B, may include resistors, capacitors 564A and 564C, and inductors used as a substrate for off-chip (rerouting to) ASIC 600. By the use of one or more ASICs 600, the active electronic components of at least a part of electronic module 111 and system 100 may be miniaturized.

Both for the feed-through filter 567 and the DC blocking element 568 (e.g., 3D silicon DC blocking capacitor technology), a substrate may be used to implement these elements. This substrate may provide the ability to combine all electrical and electronics components into a single stack mounted on top of the feed-through connection pins 511 of the LCFX connector 510 and the feed-through connection pins 521 of the HCFX connector 520 as shown in FIG. 6. This 3-layer stack, which may include ASIC 600, DC blocking element 564, and feed-through filter 567, may achieve a very high integration density to reduce the size of electrical module 500 and second module 111.

Electrical connections between layers may be provided via stud bumps 505, which are embedded into epoxy underfill 700. All active components of second module 111 (e.g., the one or more ASIC 600) and passive (e.g. feed-through filters 567 and DC blocking element 568) components of the second module 111 can be combined into a single stack. This single stack can be mounted directly on top of the connection pins 521 of the HCFX connector 520 and the connection pins 511 of LCFX connector 510.

As will be described below, these passive protection measures may not be sufficient to suppress EMI induced signals from MRI, for example. Additional components that may be used to provide further protection from strong EMI may include one or more types of clamps as discussed below with respect to FIGS. 7, 8, and 9.

Figure 7:
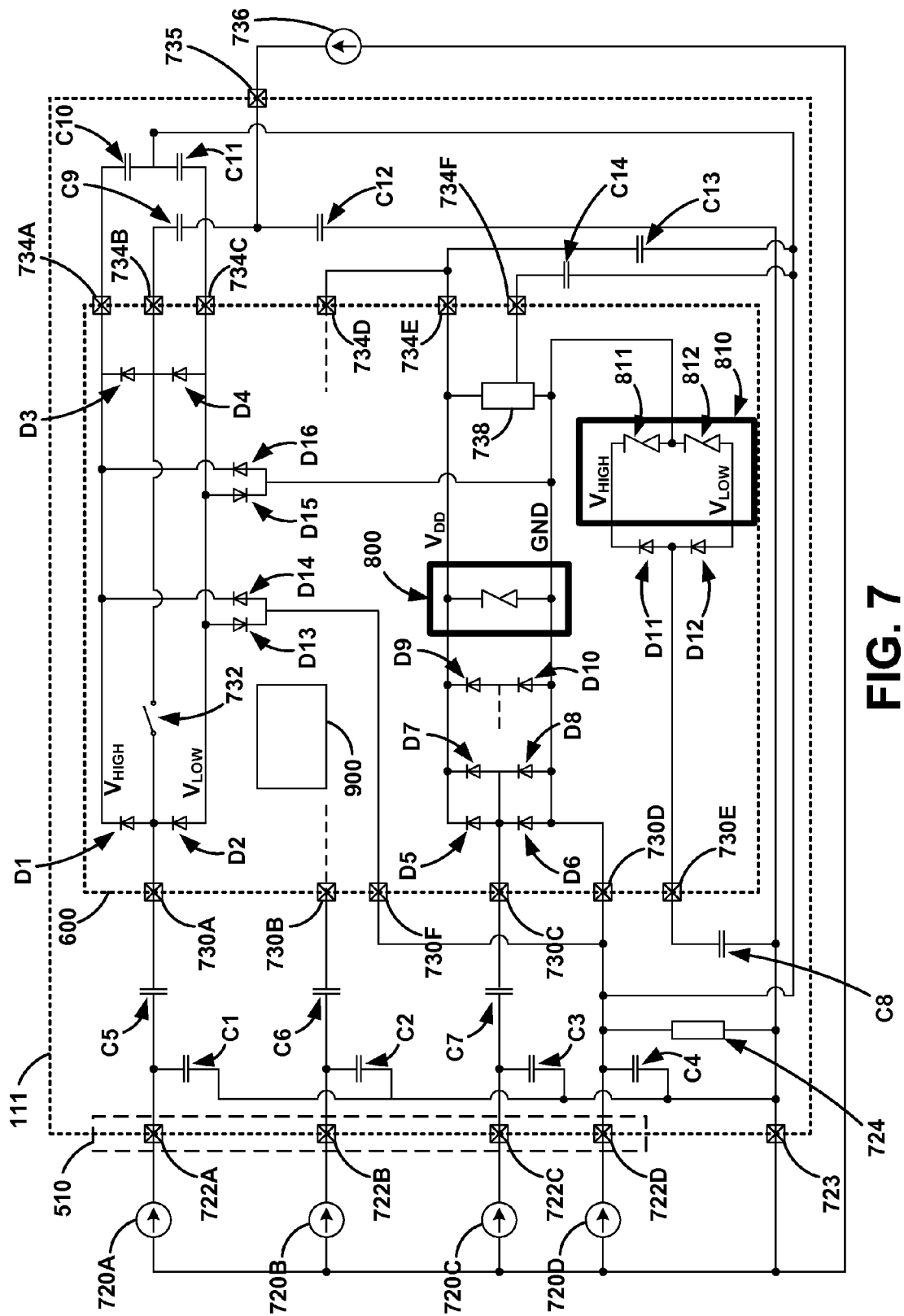
FIG. 7 is a schematic diagram of electrical components of an example electronic module that includes on-chip clamps.

FIG. 7 is a schematic diagram of electrical components of an example electronic module that includes on-chip clamps. As shown in FIG. 7, system 100 includes second module 111 which also includes ASIC 600. System 100 includes potential current sources such as current sources 720A, 720B, 720C, 720D (collectively "current sources 720") from first module 110 and current source 736 from lead 300. Second module 111 includes connectors 722A, 722B, 722C, and 722D (collectively "connectors 722") of connection 510, and connector 735 from lead 300. Connection 723 is provided to represent connection of the electronics to the housing of second module 111, and the electronics may be coupled to the housing via some impedance to the housing which is represented by resistor 724. Second module 111 also includes components that may be on or separate from ASIC 600 such as capacitors C1-C14, diodes D1-D16, and regulator 738. ASIC may also include connections 730A, 730B, 730C, 730D, 730E, 730F and connections 734A, 734B, 734C, 734D, 734E, and 734F. AISC 600 also includes EMI protection circuitry such as ESD protection circuitry that may include diodes (e.g., diodes D1-D6) and one or more clamp stages such as clamp stage 800 and clamp stage 810.

The simplified schematic of FIG. 7 only shows relevant parts, as second module 111 and ASIC 600 may include additional components not shown. The housing or casing (e.g., housing 530) of second module 111 is indicated by a dashed line. Inside the housing 530 is the integrated circuit ASIC 600 which is also indicated by a dashed line. Similar to the example of FIG. 4, there are five lines GND, PWR/CLK, COMMS, PG1, and PG2 connecting second module 111 to first module 110 via the interface cable 120. The two connectors PG1 and PG2 are only shown in a simplified manner as a single connector 722A, but there may be two connectors. The five connectors GND, PWR/CLK, COMMS, PG1, PG2 correspond to connections 722 of LCFX connector 510 of second module 111. Second module 111 may also include a 40-pin HCFX connector 520 for the lead 300, which is represented in FIG. 7 by a single connector 735 of for simplification only.

Signals PWR/CLK, COMMS and PG1/2 may correspond to signals having the following functions or characteristics. The power (PWR) and clock (CLK) line may be used to transmit a power and clock signal, which may be a bipolar square wave voltage in some examples. This same square wave may be used inside the cross-point switch matrix of second module 111 as reference clock in some examples. The rectified square wave voltage may serve as the supply voltage for the electronics of second module 111. If the rectified voltage of the power and clock line is too low to supply the electronics directly, voltage boosting may be applied directly after rectification. COMMS is a line for transferring digital data. This digital data may be used for programming the switch matrix such that signals from PG1 and PG2 are transmitted signals from first module 110 (e.g., by a signal generator or pulse generator) through second module 111 to the electrodes 132 (as selected by the switch matrix of second module 111) and receiving signals from the electrodes or other electronics of ASIC 600.

Each of the five lines GND, PWR/CLK, COMMS and PG1/2 is coupled to ground via a capacitor such as capacitors C1-C4. Each of the 40 connectors represented by connection 735 is also coupled to ground by respective capacitors represented by capacitor C12. All the capacitors represented by capacitor C12 can advantageously be feedthrough capacitors which are configured to suppress a certain amount of EMI induced current through the lines coupled to the connectors 510 and 520.

The currents induced by stronger EMI, for example by MRI RF fields, are represented by the current sources 720 and 736 which are injected in second module 111 via connectors 510 and 520. If current source 736 is the current induced through a single line of a single electrode, it should be noted that the total amount of induced current could be 40 times the current indicated by the single current source 736, assuming an example of forty electrodes and connection lines. In this same manner, induced current through connection 722A would be two times that indicated by current source 720A when two distinct pulse generator lines are represented by the single current source of FIG. 7. DC blocking capacitors C5-C7 and C9 may be coupled between the pins PWR/CLK, COMMS, PG1/2 (represented by connections 722) and connection 735 and respective connections 730A, 730B, 730C, and 734B of the ASIC 600. Capacitors C9 and C12 may represent separate capacitors provided for each electrode connected to second module 111 via connection 735. In other words, each electrode may be coupled to a respective capacitor C9 and C12.

The signals propagating over lines PG1/2 via connections 722A and 730A are basically fed to the forty electrodes 132 (shown in FIG. 3 and FIG. 4) via a switch matrix SM and connections 735 and 734B, and vice versa. Switch matrix 732 is only represented by a single switch for simplification only. However, in practice, switch matrix 732 may instead include any number of switches needed to selectively couple any of electrodes 132 to any of the pulse generator lines and/or ground. The switch matrix is programmed in accordance with the requirements of the various possible applications of neurostimulation and/or neurorecording, such as for DBS in some examples.

ASIC 600 may also include one or more ESD protection circuits, such various diodes that may be coupled to the bond pad. These diodes may be coupled in parallel to other clamps such as clamp stages 800, 811, and 812. Each signal line from connections 730A, 730B, 730C, and 734B may be internally protected by respective ESD protection circuitry. Each ESD protection circuit may include two diodes out of the diodes D1-D10. For the signal lines power clock (connection 730B) and comm (connection 730C), at least one diode is coupled in forward direction from system ground GND (and connection 730D) to the respective signal line and at least one diode is coupled from the respective signal line to supply voltage line $V_{DD}$. $V_{DD}$ may have a voltage level corresponding to the voltage supply levels of various voltage supply domains. The pulse generator lines through connection 730A and the electrode lines through connection 734B may also be protected by ESD protection diodes (simplified in FIG. 7 by diodes D1, D2, D3, and D4). Protection diodes D13, D14, D15, and D16 are coupled between supply voltage lines $V_{LOW}$ and $V_{HIGH}$ of the voltage domain that may have greater supply voltage levels (positive $V_{HIGH}$ and negative $V_{LOW}$) than supply voltage domain $V_{DD}$.

In addition, the connections/connectors at the ASIC 600 casing, such as connections 730A, 730B, 730C, 730D, 730E, 730F and connections 734A, 734B, 734C, 734D, and 734E may also represent approximate positions of the respective bond pads of the ASIC 600 with respect to the other components.

ASIC 600 may also include voltage regulator 738 (e.g., a low drop out (LDO) voltage regulator) configured to stabilize $V_{DD}$ and one or more capacitors C1-C5. ASIC 600 may also include connection 734F for voltage regulator 738 and resistor 724. Block 900 represents other components of ASIC 600, such as active and passive parts/components/devices integrated on the ASIC 600, that may not be directly pertinent to the discussion of EMI protection devices described herein. In other words, ASIC 600 and second module 111 may include additional components not shown in FIG. 7.

In addition, clamp stage 800 (e.g., a low voltage MRI clamp), clamp stage 811 (e.g., a high voltage MRI clamp), and clamp stage 812 (e.g., a high voltage MRI clamp) may be coupled between the supply voltage lines of the different supply voltage domains $V_{DD}$, $V_{HIGH}$, $V_{LOW}$, and system ground (e.g., GND). In particular, first clamp stage 800 may be coupled between the supply voltage line $V_{DD}$ of this supply voltage domain and system ground GND. There is further a clamp stage 810, which may include two different clamp stages 811 and 812, coupled between the supply voltage line $V_{HIGH}$ and system ground GND and supply voltage line $V_{LOW}$ and system ground GND, respectively. Although claim stages 800, 811, and 812 may be coupled between a supply domain and ground, in other examples, one or more clamp stages may be coupled between two supply domains having different voltages and/or currents.

A part of the excess currents from current sources 720 and 736 due to strong EMI fields like those caused by MRI may be deviated via the EMI capacitors C1-C4 and C12, but a lot of current may still remain and propagate to the supply voltage lines of the supply voltage domains without further intervention. This remaining excess current may be absorbed by the clamp stages 800, 811, and 812 (e.g., different MRI clamps) on each of the supply domains of ASIC 600. Clamp stages 800, 811, and 812 may be added to each of the ASIC supply (rail) domains: clamp stage 810 (or more specifically clamp stages 811 and 812) for the high-voltage domains $V_{HIGH}$ and $V_{LOW}$ and clamp stage 800 for the low-voltage domain $V_{DD}$.

In an advantageous embodiment, the respective ESD diodes, for example, D5 and D6 can be enlarged. In other words, diodes D5 and D6 can be configured for higher currents. Furthermore, the involved metal tracks related to diodes D5 and D6 can be widened to reduce the resistance for higher currents. These configurations of ASIC 600 can support the excess current (e.g., from current sources 720 and 736) due to MRI (or other very strong fields) and keep this excess current from the core of ASIC 600. In other words, these diodes may absorb some of the injected energy instead of energy being directed to sensitive portions of ASIC 600. Part of the MRI RF current injection (current sources 720 and 736) into second module 111 may be returned to the casing of second module 111 via the EMI capacitors C1-C4 and C12 on all pins (except GND) and the remainder is absorbed by clamps 800, 811, and 812 on all supply domains.

Clamp stages 800, 811, and 812 may be distinguished from the ordinary ESD circuitry, (such as diodes D5 and D6). ESD circuitry typically only handles high but short duration (e.g., in the nanosecond (ns) range) currents due to an electrostatic discharge. In contrast, the MRI induced RF current bursts can last orders of magnitude longer (microseconds (μs) to milliseconds (ms) with potentially comparable current levels (e.g., sometimes up to and greater than one Ampere)). Therefore, the special clamp stages (e.g., clamp stages 800 and 810) according to the aspects and examples of the disclosure may provide EMI protection where typical ESD circuits cannot. Additional changes may be made to the bond pad ring in order to cope with MRI induced currents and voltages.

Clamps 800, 811, and 812 may also be effective against MRI gradient field induced overvoltage stress by limiting the maximum voltage on all supply domains. Thus, the clamps can keep the electronics core of ASIC 600 within typical safe operating area (SOA). In addition, clamp stages 800, 811, and 812 also are configured to protect components which are external to ASIC 600 from overvoltage and/or overcurrent stress.

In some examples, clamps 800, 811, and 812 are configured to not trigger when the ASIC 600 is in its normal operation mode. In other words, the clamps will not absorb current during operations in which ASIC 600 is providing stimulation and/or recording functions. If the low on-resistance of any of clamp stages 800, 811, or 812 were active, the clamp stages would introduce a load on the supply rails of ASIC 600 that would likely be too high for an ultra-low power design of second module 111 and system 100. Activation of any clamps during normal operation may cause malfunction of certain functions due to a lack of power and/or quickly drain power from the power supply of system 100.

In one example, the electronics of second module 111 (other parts in block 900 of ASIC 600 and one or more external components not shown in FIG. 7) are switched-off when the implant/probe 130 (second module 111 and ASIC 600) undergoes very strong EMI, such as would occur during an MRI scan. This mode may be referred to as an MRI mode. The switch off may be controlled by first module 110 via user interaction and/or by way of automated detection of strong fields indicative of an MRI scan. However, the on-chip rectification of the (MRI) induced RF currents may lead to rising power supply line voltages and the clamp stages integrated on the ASIC 600 stem this rise by absorbing any excess current. Accordingly, the electronics module 111 (and/or any other modules of system 100) can be configured to have two operating modes: a first, normal operating mode for neurostimulation and/or neurorecording and a second, high-EMI (or MRI) operating mode in which the electronics for normal operation of the ALC 111 are switched off.

In one example, the different clamp stages for the different supply voltage domains ($V_{DD}$ and $V_{HIGH}$, $V_{LOW}$ etc.) may have different configurations. For example, the clamp stage(s) for relatively high voltage supply voltage domains ($V_{HIGH}$ and $V_{LOW}$) can be of a first type while the clamp stage(s) for supply voltage domains having supply voltage levels relatively lower than those of the high voltage supply voltage domains may be of a second type.

In some examples, the clamp stages 800, 811, and/or 812 are not directly connected to the bond pads of ASIC 600 but only via a set of diodes (for example diodes D5 and D6). This connection via the diodes may prevent the bond pad itself from being loaded in normal operation with the relatively large clamp structures. In addition, in this way, a single clamp stage may be configured to absorb current and/or voltage from the voltage domain it is connected to.

As shown in FIG. 7, the relative position of the various components, stages, devices, etc. in terms of electrical interconnection may substantially contribute to the advantages of the present disclosure. In this regard, the EMI inducing lines are shown as being external to the housing of second module 111. The various signal lines penetrate the housing of second module 111 and are then first capacitively coupled to ground by EMI capacitors C1-C4 and C12 which are configured to remove a certain amount of EMI induced voltages/currents. EMI capacitors C1-C4 and C12 (which represents a separate capacitor for each electrode of lead 300 connected via connection 735) represent capacitors directly mounted to the feedthrough pins of each connection. Capacitors C1-C4 and C12 may be part of feed-through filter 567 of FIG. 6. The signal lines are then coupled to DC blocking capacitors which are located between the EMI capacitors C1-C4 and the input/output pins of the ASIC 600. The next elements encountered by the signals (in a direction from the outside to the inside of second module 111 and ASIC 600) are bond pads of the ASIC 600. After the bond pads, there are the ESD circuits/diodes (e.g., diodes D5 and D6) and only after the ESD circuits/diodes are the clamp stages 800, 811, and 812 that are located for absorbing the remaining excess current. In some examples, the diodes may be coupled in parallel to one or more clamp stages 800, 811, and 812. The sequence of elements/stages from outside second module 111 towards the inside of ASIC 600 and towards the clamp stages 800, 811, and 812, is therefore the following: (1) signal line (as the EMI inducing element), (2) connector at the housing of second module 111, (3) EMI capacitors (or more complex EMI filters) between signal line and ground, (4) DC blocking capacitors, (5) bond pads, (6) ESD protection diodes, (7) supply voltage lines, and (8) clamp stages (e.g., clamp stages 800, 811, and 812).

Figure 8:
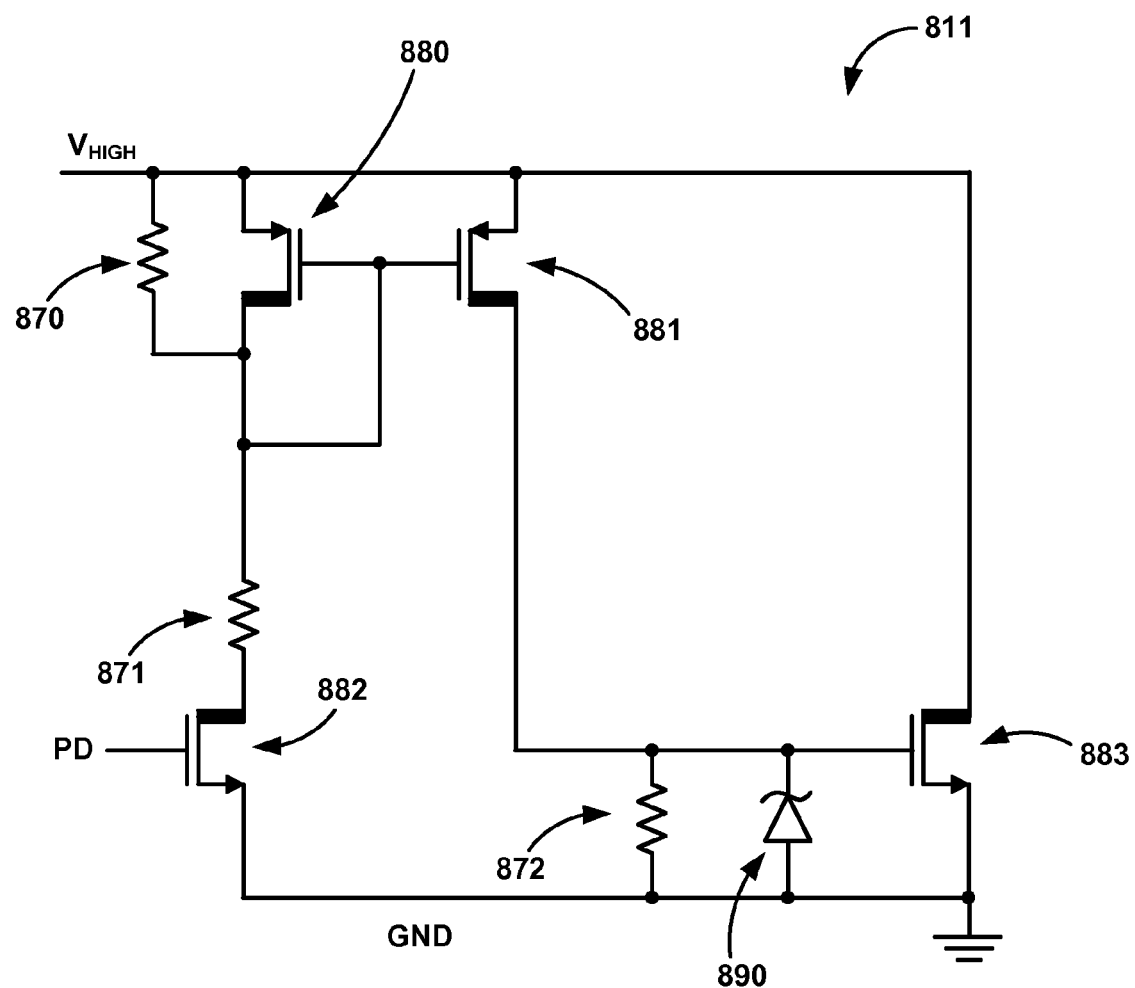
FIG. 8 is a schematic diagram of a first clamp stage type for absorbing excess power.

FIG. 8 is a schematic diagram of an example first clamp stage type 811 of clamp stage 810 for absorbing excess power. Although clamp stage type 811 is described in FIG. 8, the same type of circuit may be used as clamp stage 812 and coupled between $V_{LOW}$ and GND (exchanging GND by $V_{LOW}$ and $V_{HIGH}$ by GND in FIG. 8) and then serve as clamp stage 812. The clamp stage 811 may be of a first type and include four high voltage MOSFET transistors 880, 882, 881, and 883, three resistors 870, 871, and 872, and a Zener diode 890. Transistor 880 is diode coupled. The source of transistor 880 is coupled to the supply voltage line (rail) $V_{HIGH}$ having the more positive potential. Gate and drain of transistor 880 are coupled together (diode coupled). The source of transistor 881 is also coupled to the supply voltage line $V_{HIGH}$, the gate of transistor 881 is coupled to the gate of transistor 880, and the drain of transistor 881 is coupled to the gate of transistor 883. Transistors 880 and 881 are coupled as a current mirror, mirroring the current through transistor 880 to 881. An appropriate factor for the magnitudes of the currents can be chosen by the ratio of the widths of the channels of transistors 880 and 881. A resistor 870 is coupled parallel to the channel of transistor 880, i.e. one side of resistor 870 is coupled to $V_{HIGH}$ and the other side is coupled to the drain of transistor 880. A second resistor 871 is coupled with one side to the drain of 880 and with another side to the drain of transistor 882. The source of transistor 882 is coupled to ground GND. The gate of transistor 882 receives a control signal PD (power down) for switching this transistor 882 on and off (e.g., the on and off state of the clamp stage). Transistor 883 is coupled with its drain to $V_{HIGH}$ and with its source to GND. A third resistor 872 and the Zener diode 890 are coupled in parallel and both between the gate of transistor 883 and ground GND.

Generally, the PD signal is low in normal operation of ASIC 600 and increased to high when the positive supply voltage rail $V_{HIGH}$ nears its SOA limit. If the signal PD is high (logic high level or sufficiently positive potential with respect to GND, gate-source voltage of transistor 882 greater than threshold voltage of transistor 882) then transistor 882 is switched on (i.e., the channel of transistor 882 is conducting). This means that two current paths are present between $V_{HIGH}$ and GND: a first one through resistors 870 and 871 and transistor 882 and a second one through transistor 880, resistor 871, and transistor 882. Dependent on the voltage difference between $V_{HIGH}$ and GND, a rather small current may first flow through resistors 870 and 871 and transistor 882 (due to the fact that two MOSFET threshold voltage levels are required to drive a current through the channels of the two transistors 880 and 882). However, if $V_{HIGH}$ is high (positive versus GND) enough, any current through transistor 880 is mirrored to transistor 881 and from there fed to the gate of transistor 883. This configuration provides that transistor 883 is also switched on as soon as the voltage across resistor 872 reaches the threshold voltage of transistor 883. Transistor 883 can be designed for high currents and high voltages and then constitute a very high (shunt) load for the supply voltage level $V_{HIGH}$. This high load can prevent $V_{HIGH}$ from reaching potentially undesirable voltage levels that could damage other components of ASIC 600. Zener diode 890 may prevent the gate-source voltage of transistor 883 from becoming too high that could destroy or damage transistor 883.

Figure 9:
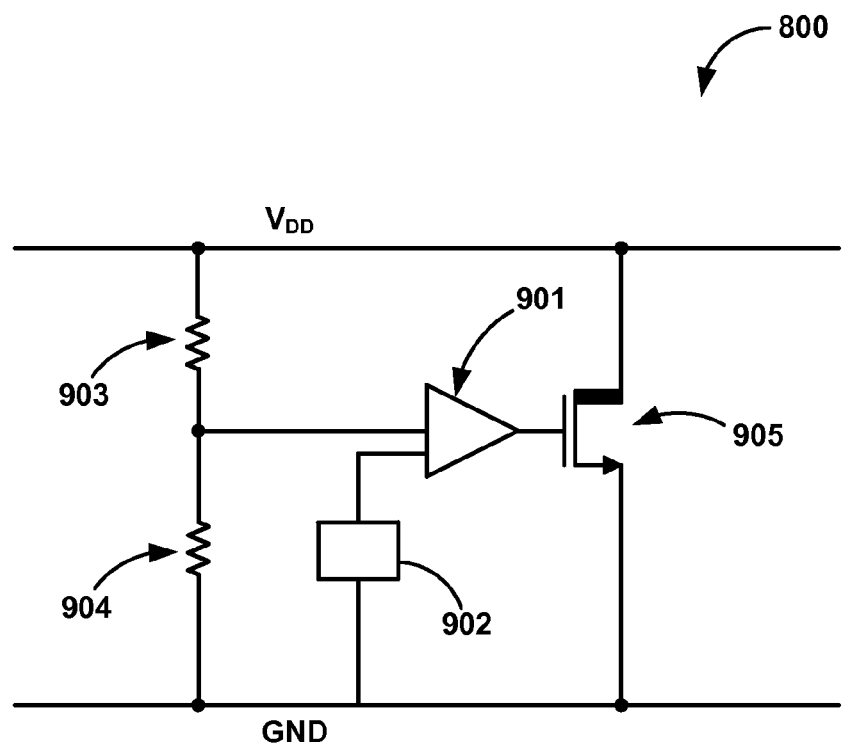
FIG. 9 is a schematic diagram of a second clamp stage type for absorbing excess power.

FIG. 9 is a schematic diagram of an example second clamp stage type 810 for absorbing excess power. Clamp stage 800 (e.g., a low voltage clamp stage) of a second type may be coupled between the low-voltage supply line $V_{DD}$ (low-voltage supply domain). This clamp stage of the second type can be realized with an operational transconductance amplifier (OTA) 901 based shunt regulator circuit that is configured to compare the actual voltage on the low voltage supply domain $V_{DD}$ with a threshold reference voltage. The threshold reference voltage may be higher than the low-voltage supply voltage in normal operating mode of ASIC 600 and still below the safe operating area (SOA) of ASIC 600. The supply voltage $V_{DD}$ can be fed to an input of the OTA through a resistor divider of resistor 903 and resistor 904. If the supply voltage $V_{DD}$ gets too high, the clamp stage 800 (shunt regulator) switches on and starts absorbing any excess current on this supply domain by turning on transistor 905. The reference voltage can be generated by a bandgap circuit 902 that is activated together with the shunt regulator when the supply exceeds the (still low) Power-On-Reset (POR) threshold voltage level. If the shunt regulator is configured to be fast enough, the shunt regulator (e.g., clamp stage 800) may be able to absorb excess energy associated with the spiking voltage peaks due to MRI gradient fields.

Figure 10:
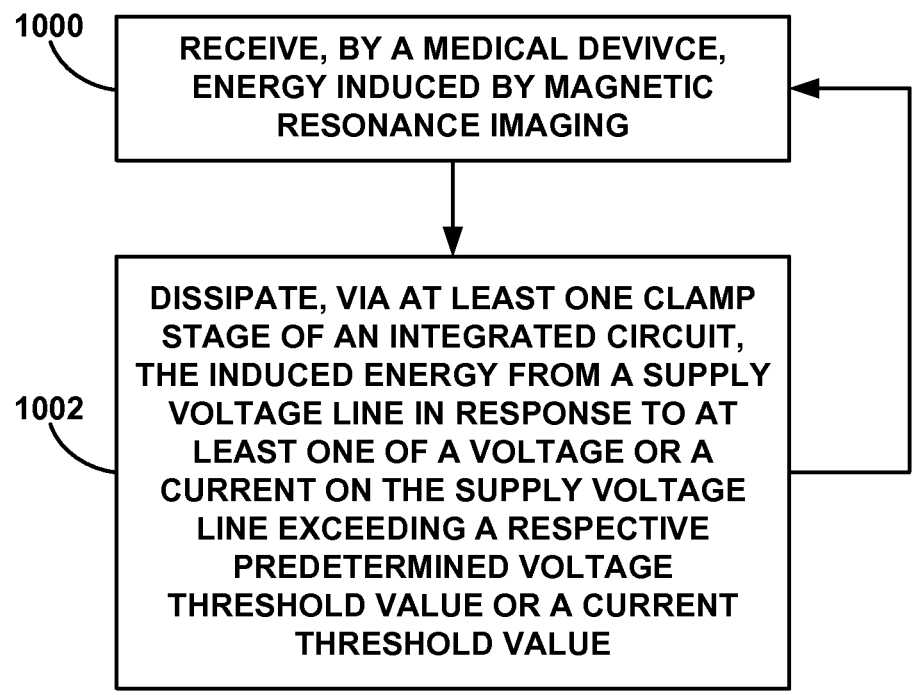
FIG. 10 is a flow diagram of an example technique for dissipating EMI induced energy.

FIG. 10 is a flow diagram of an example technique for dissipating EMI induced energy such as MRI induced energy. The technique of FIG. 10 may be implemented in any systems and modules described herein, such as system 100, first module 110, and second module 111. However, second module 111 and ASIC 600 will be described herein. A medical device, such as system 100, may receive energy induced by MRI (1000). This energy may be induced via one or more electrical wires or connections from MRI fields or other such sources. One or more clamp stages (e.g., clamp stages 800, 811, and/or 812) that are a part of an integrated circuit (e.g., ASIC 600) may dissipate the induced energy from a supply voltage line in response to at least one of a voltage or a current on the supply voltage line exceeding a respective predetermined voltage threshold value or a current threshold value (1002). In this manner, the one or more clamp stages, alone or together, may absorb excess energy and keep that excess energy from damaging components of the integrated circuit that includes the one or more clamp stages. As described herein, the at least one clamp may dissipate energy from a supply voltage or current line to another supply voltage or current line or to ground.

In addition, it should be noted that system 100 may not be limited to treatment or monitoring of a human patient. In alternative examples, system 100 may be implemented in non-human patients, e.g., primates, canines, equines, pigs, and felines. These other animals may undergo clinical or research therapies that my benefit from the subject matter of this disclosure.

Figure 11:
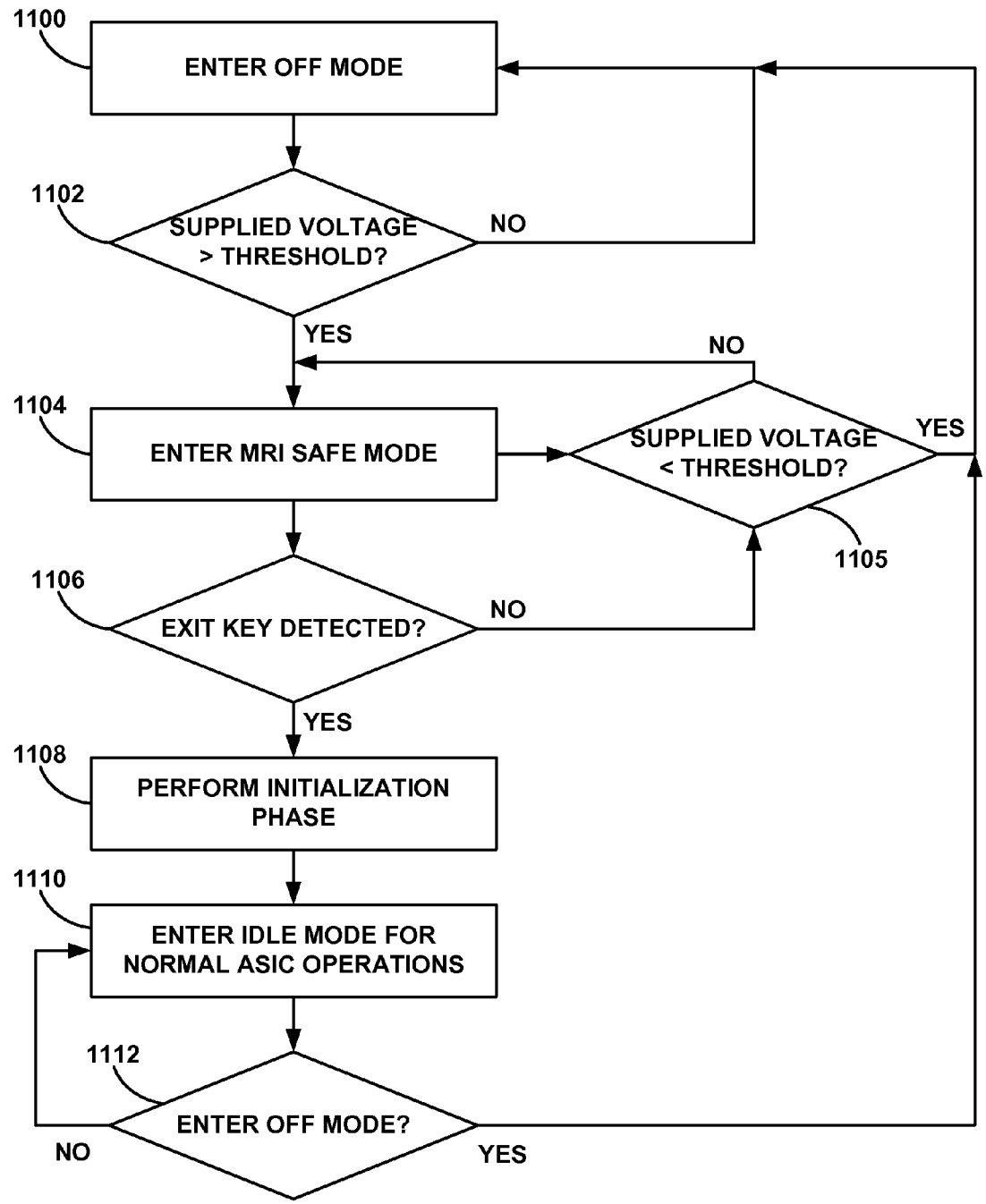
FIG. 11 is a flow diagram of an example technique for entering and/or exiting an MRI safe mode for a medical device.

FIG. 11 is a flow diagram of an example technique for entering and/or exiting an MRI safe mode for a medical device such as one or more modules of system 100. The technique of FIG. 11 will be described with regard to ASIC 600 of second module 111 and first module 110 of system 100, but the technique may be used for other devices as well. ASIC 600, and any other integrated circuits of second module 111, for example, can be configured into a variety of different modes. For example, ASIC 600 may be configured to be in an Off Mode, an MRI Safe Mode, an Initialization Phase, and an Idle Mode. As described further below, ASIC 600 may be switch off during the Off Mode and the MRI Safe Mode. ASIC 600 may be configured to initialize processes from a memory during the Initialization Phase, and ASIC 600 may enter an Idle Mode with could be described as the normal operating mode. ASIC 600 may perform various functions or enter other modes, such as modes related to delivering neurostimulation, recording physiological signals, or any other functions. The manner in which ASIC 600 can switch between each mode is described in more detail in FIG. 11.

From any function or mode, ASIC 600 may enter the Off Mode (1100) although specific branches may not be shown in FIG. 11. ASIC 600 may enter or reside in the Off Mode when ASIC 600 does not receive a power and/or clock signal from first module 110 or the power and/or clock signal is too low to generate a sufficiently high rectifier output voltage (e.g., the power supply voltage for ASIC 600). ASIC 600 may include an undervoltage lockout (UVLO) circuit that resets all digital circuits until the rectifier voltage is sufficiently high for the digital logic of ASIC 600 to again work properly. During the Off Mode, all clamp stages (which may include EMI protection circuits in addition to MRI clamp stages) may be on or activated such that excess energy applied to the supply lines of ASIC can be dissipated by the clamp stages described herein. If ASIC 600 and/or first module 110 does not receive a supplied voltage greater than or exceeding a threshold voltage level (e.g., sufficient voltage to operate) ("NO" branch of block 1102), ASIC 600 may remain in the Off Mode (1100). Although the supplied voltage and corresponding threshold voltage level is described in this example, other domains could be used, such as the current domain or power domain of the received electrical signal.

If ASIC 600 and/or first module 110 does receive supplied voltage exceeding the threshold voltage level ("YES" branch of block 1102), ASIC 600 may enter the MRI Safe Mode (1104). The supplied voltage exceeding the threshold voltage level (which could be a power level or current level in other examples) may be provided as a normal operational power signal from first module 110 or caused by RF signals or gradients generated in an MRI machine, for example. In some examples, ASIC 600 may transition to MRI Safe Mode when the rectifier output supply becomes larger than the UVLO circuit threshold (during which time the ASIC 600 is powered). The UVLO may release the reset under two conditions: (1) in response to a power/clock signal from first module 110 with a sufficiently high voltage for normal operation or (2) in response to injected MRI induced AC currents rectified into an ASIC power supply voltage above the UVLO threshold. In other examples, first module 110 and/or ASIC 600 may include a Hall sensor configured to detect strong static MRI fields indicating that the MRI Safe Mode (or Off Mode) should be entered.

When ASIC 600 is in MRI Safe Mode, most ASIC blocks are disabled to prevent operation of ASIC 600 and interference with MRI imaging process and the one or more clamp stages are enabled or activated to prevent low and high voltage supply lines of ASIC 600 from being pushed beyond the Safe Operating Area (SOA) voltage limits by the injected MRI current. ASIC 600 may still be able to receive sufficient power from the rectifier circuit to start even though a low voltage clamp stage (e.g., clamp stage 812) because, despite a very abrupt impedance curve between the activated and deactivated modes, enough current or voltage can remain on the low voltage supply rail. If the supplied voltage to ASIC 600 drops below the threshold power level ("YES" branch of block 1105), ASIC 600 may revert back to the Off Mode (1100). If the supplied voltage to ASIC 600 stays above the threshold power level ("NO" branch of block 1105), ASIC 600 may remain in the MRI Safe Mode (1104). Even if ASIC 600 can receive enough power to start during MRI Safe Mode, ASIC 600 will still not power up without receiving an exit key from first module 110 (e.g., a main electronic module). Therefore, if ASIC 600 does not receive an exit key ("NO" branch of block 1106), ASIC 600 will also remain in MRI Safe Mode (1104).

If ASIC 600 does detect or receive an exit key ("YES" branch of block 1106), ASIC 600 performs the initialization phase to start up (1108). The exit key may be a key or code, such as a digital bit string, that is highly unlikely to be duplicated from signals generated by an MRI machine. Since lead 300, connecting cable 120, or any other electrical wires may act as an antenna for the RF fields from the MRI machine, signals may be generated within system 100 and act like signals between first module 110 and second module 111. Therefore, the exit key may be a specific signal or code required by ASIC 600 to exit the MRI Safe Mode. In other words, signals induced by the MRI machine may not be able to cause ASIC 600 from starting up. Therefore, the exit key can prevent ASIC 600 activity during an MRI scan that could interfere with the image reconstruction used by the MRI machine from signals detected from the patient. In some examples, the exit key may be a 32 bit string, such as a DC neutral 32 bit string: 1110 1000 1101 0100 1011 1100 0100 1001. ASIC 600 may receive the exit key over the coms line from first module 110. The exit key may be randomly generated in some examples.

After the MRI fields induce power build up in ASIC 600, the supply voltage drops in response to the MRI fields being removed. After removal of the MRI fields, ASIC 600 may return to the Off Mode. In the OFF and MRI Safe Mode, no oscillators or clocks are enabled so ASIC 600 does not generate any AC signals that could interfere with MRI imaging. In other words, ASIC 600 would not produce any interference or harmonics at 64 MHz for 1.5 T machine, for example, radiating from ASIC 600 via lead 300 and/or cable 120 (which may act as antennas). As discussed in FIG. 12, the power/clock recovery circuit may provide further prevention of MRI interference from ASIC 600.

Once ASIC 600 receives the correct exit key, ASIC 600 exits the MRI Safe Mode and transitions to the initialization phase (1108). During the initialization phase, ASIC 600 may download some or all of the One-Time Programmable (OTP) non-volatile memory and may mirror this data into the volatile ASIC registry (e.g., data such as trim and calibration data). ASIC 600 may perform error checking on the data downloaded during the initialization phase. When no errors are present, ASIC 600 enters the Idle Mode for normal ASIC operations (1110). The Idle Mode may be the default mode for ASIC 600 during which ASIC 600 may launch into other functional modes such as a stimulation mode, recording mode, resistance mode for measurements, and other modes. As long as ASIC 600 receives sufficient power or does not detect MRI fields ("NO" branch of block 1112), ASIC 600 continues to operate in Idle Mode or other functional modes. If ASIC 600 is to enter the Off Mode ("YES" branch of block 1112), such as if power is no longer sufficient, ASIC 600 enters the Off Mode (1100).

Figure 12:
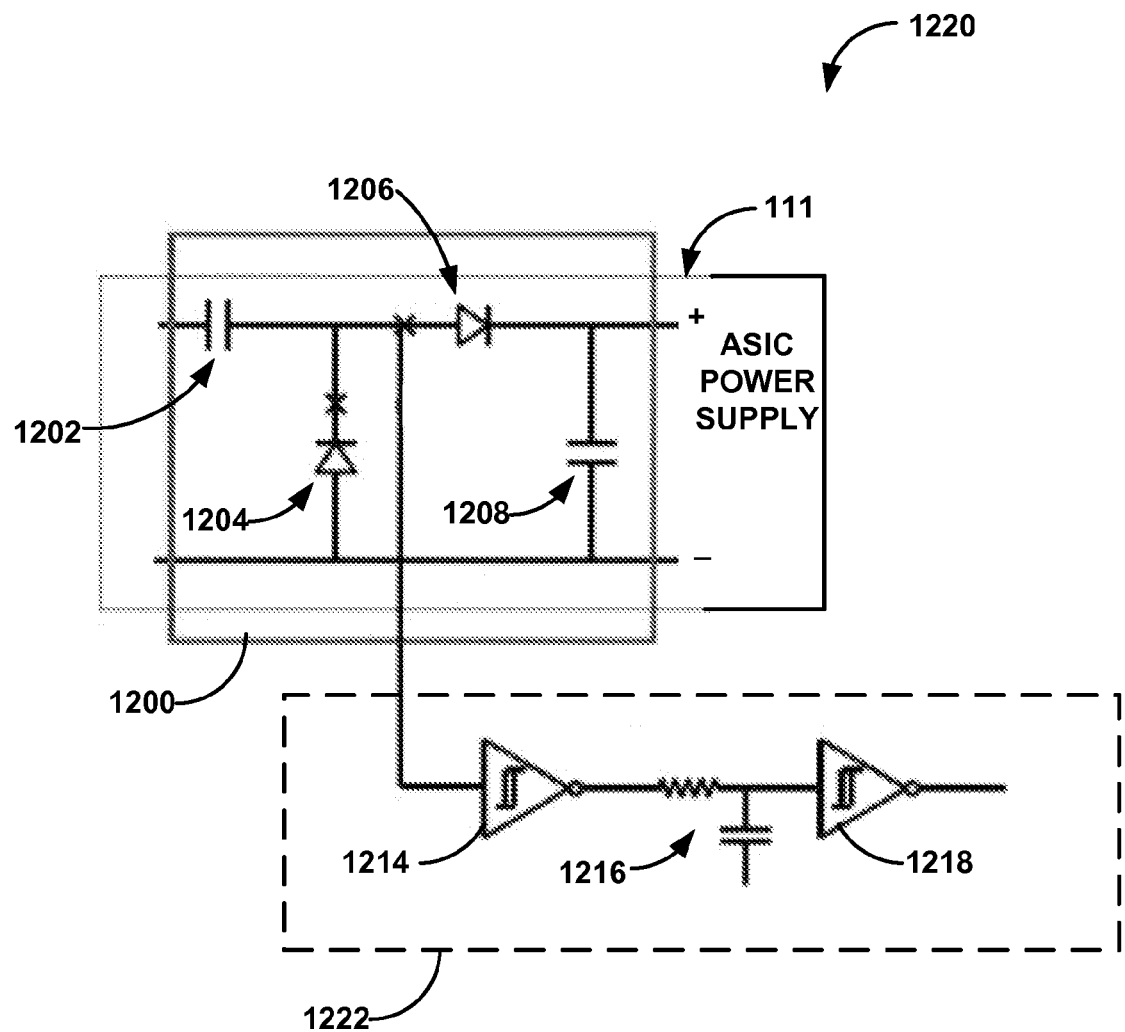
FIG. 12 is a schematic diagram of electrical components of an example rectifier and clock recovery circuit for a medical device.

FIG. 12 is a schematic diagram of electrical components of an example rectifier circuit 1200 and clock recovery circuit for a medical device. As shown in FIG. 12, recovery circuit 1220 includes rectifier 1200 and clock recovery circuit 1222, which may be disposed within second module 111. Rectifier circuit 1200 may include capacitors 1202 and 1208 (which is a reservoir capacitor that is continually monitored) and diodes 1204 and 1206. Recovery circuit 1220 may thus provide power to the electronics of second module 111 such as ASIC 600. The AC signal is sent to clock recovery circuit 1222, e.g., through Schmitt trigger 1214, followed by MRI filter 1216, and then followed by another Schmitt trigger 1218 to generate a digital clock signal that is not affected by the surrounding MRI field or any other source of interference (e.g., interference from a mobile phone). MRI filter 1216 may be a low pass filter (e.g., include a resistor and a capacitor) tuned to a certain frequency. In some examples, the frequency may be less than the frequencies to which the MRI machine is sensitive (e.g., 64 MHz for a 1.5 T MRI machine). In one example, the MRI filter may be a low pass filter that passes frequencies less than 1 MHz. However, lower or higher frequency filters may be used in other examples. The frequencies passed by filter 1216 may be less than those that may cause interference with MRI operation. For example, ASIC 600 may operate at a frequency of approximately 100 kHz, which is an order of magnitude less than a low pass filter set to 1 MHz, as one example. The low pass filter may be set based on the normal operating frequency of second module 111 and/or other considerations such as possibly interfering frequencies to other external devices.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules (e.g., modules 110 and 111) and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. An implantable electronic device, the device comprising:
    a housing;
    at least one connector coupled to the housing and configured to at least one of receive first electrical signals or transmit second electfical signals; and
    an integrated circuit disposed within the housing, wherein the integrated circuit comprises a first clamp stage coupled to a first supply voltage line of a first voltage domain of the integrated circuit and a second clamp stage different than the first clamp stage, wherein the first clamp stage is configured to dissipate magnetic resonance imaging (MRI) induced energy from the first supply voltage line in response to at least one of a voltage or a current on the first supply voltage line exceeding a respective predetermined voltage threshold value or a current threshold value, and wherein the first clamp stage is configured to be coupled to the first supply voltage line and the second clamp stage is configured to be coupled to a second supply voltage line of a second voltage domain.

2. The device of claim 1, further comprising at least one feedthrough filter element disposed within the housing and coupled between feedthrough pins of the at least one connector and the housing.

3. The device of claim 1, wherein the at least one feedthrough filter element comprises one or more capacitors, resistors, or inductors.

4. The device of claim 1, wherein the first clamp stage comprises at least one energy dissipating element.

5. The device of claim 4, wherein the at least one energy dissipating element comprises at least one of a variable resistor, or a transistor, or a clamping diode.

6. The device of claim 1, wherein the first clamp stage is configured as a shunt regulator.

7. The device of claim 1, further comprising an electrostatic discharge (ESD) protection circuitry, wherein the ESD protection circuitry is coupled in parallel to the first clamp stage.

8. The device of claim 7, wherein the ESD protection circuitry comprises a diode disposed between a bond pad and the first supply voltage line, and wherein the diode is reversely biased during normal operation of the device.

9. The device of claim 1, wherein a first magnitude of a first supply voltage level of the first supply voltage domain is greater with respect to system ground than a second magnitude of a second supply voltage level of the second supply voltage domain.

10. The device to claim 1, wherein at least one of the first clamp stage or the second clamp stage is configured to switch between a first state and a second state, and wherein the at least one of the first clamp stage or the second clamp stage is not operable to dissipate energy in the first state and is operable to dissipate energy in the second state in response to a supply voltage on the first supply voltage line exceeding a normal operational voltage of the first supply voltage line.

11. The device of claim 1, wherein the first clamp stage comprises one or more high voltage metal-oxide-semiconductor field-effect transistor (MOSFET) transistors.

12. The device of claim 1, wherein the second clamp stage comprises:
    an operational transconductance amplifier (OTA) comprising a first input, a second input, and an output;
    a reference source configured to provide a threshold signal for the first input of the OTA; and
    a transistor coupled between the second supply voltage line and a ground, wherein the second input of the OTA is coupled to the second supply voltage line and the output of the OTA is coupled to one of a base or a gate of the transistor to switch the transistor on when a voltage level of the second supply voltage line exceeds the threshold signal provided by the reference source.

13. The device of claim 1, wherein the first clamp stage is coupled between the first supply voltage line and one of the second supply voltage line or a third supply voltage line, and wherein the first supply voltage line has a voltage different than the second supply voltage line or the third supply voltage line to which the first clamp stage is coupled.

14. The device of claim 1, wherein the first clamp stage is coupled between the first supply voltage line and a system ground line of the implantable electronic device.

15. The device of claim 1, wherein the housing is a first housing, and wherein the integrated circuit is configured to at least one of receive the first electrical signals from or transmit second electrical signals to a main electronic device within a second housing distinct from the first housing via the at least one connector.

16. The device of claim 1, wherein the at least one connector is a first one or more connectors, the device further comprising a second one or more connectors configured to electrically couple to a medical lead carrying a plurality of electrodes.

17. The device of claim 1, wherein the integrated circuit is configured to enter a safe mode upon receiving a supplied voltage exceeding a threshold voltage, and wherein the integrated circuit is configured to exit the safe mode only upon receiving an exit key from a main electronic device.

18. The device of claim 17, wherein the first clamp stage is activated during the safe mode, and wherein the first clamp stage is deactivated in response to exiting the safe mode.

19. A system comprising:
a first electronic module comprising a first housing;
a second electronic module comprising:
a second housing distinct from the first housing;
a first connector coupled to the first housing and configured to at least one of receive first electrical signals from or transmit second electrical signals to the first electronic module;
an integrated circuit disposed within the second housing, wherein the integrated circuit comprises a first clamp stage coupled to a first supply voltage line of a first voltage domain of the integrated circuit and a second clamp stage different from the first clamp stage, and wherein the first clamp stage is configured to dissipate magnetic resonance imaging (MRI) induced energy from the first supply voltage line in response to at least one of a voltage or a current on the first supply voltage line exceeding a respective predetermined voltage threshold value or a current threshold value, and wherein the first clamp stage is configured to be coupled to the first supply voltage line and the second clamp stage is configured to be coupled to a second supply voltage line of a second voltage domain; and
a second connector; and
a medical lead comprising a plurality of electrodes and configured to be electrically coupled to the second electronic module via the second connector.

20. The system of claim 19, wherein the first electronic module comprises a pulse generator configured to provide electrical stimulation pulses to the second electronic module.

21. The system of claim 19, wherein the second electronic module comprises a switch matrix that selectively couples one or more electrodes of the plurality of electrodes to the pulse generator of the first electronic module.

22. The system of claim 19, wherein the system is configured to deliver deep brain stimulation via one or more of the plurality of electrodes.

23. The system of claim 19, wherein the second electronic module further comprises an electrostatic discharge (ESD) protection circuitry, and wherein the ESD protection circuitry is coupled in parallel to the first clamp stage and comprises a diode disposed between a bond pad and the first supply voltage line, and wherein the diode is reversely biased during normal operation of the second electronic module.

24. The system of claim 19, wherein a first magnitude of a first supply voltage level of the first supply voltage domain is greater with respect to system ground than a second magnitude of a second supply voltage level of the second supply voltage domain.

25. The system to claim 19, wherein at least one of the first clamp stage or the second clamp stage is configured to switch between a first state and a second state, and wherein the at least one of the first clamp stage or the second clamp stage is not operable to dissipate energy in the first state and is operable to dissipate energy in the second state in response to a supply voltage on the first supply voltage line exceeding a normal operational voltage of the first supply voltage line.

26. The system of claim 19, wherein the second clamp stage comprises:
an operational transconductance amplifier (OTA) comprising a first input, a second input, and an output;
a reference source configured to provide a threshold signal for the first input of the OTA; and
a transistor coupled between the second supply voltage line and a ground, wherein the second input of the OTA is coupled to the second supply voltage line and the output of the OTA is coupled to one of a base or a gate of the transistor to switch the transistor on when a voltage level of the second supply voltage line exceeds the threshold signal provided by the reference source.

27. A system comprising:
means for receiving first electrical signals from a first electronic module comprising a first housing and by a second electrical module comprising a second housing distinct from the first housing; and
an integrated circuit within the second housing of the second electrical modules, wherein the integrated circuit comprises:
means for supplying a first voltage for the integrated circuit;
means for supplying a second voltage for the integrated circuit;
means for providing a ground for the integrated circuit;
means for, responsive to at least one of a voltage or a current on the means for supplying the first voltage exceeding a respective predetermined voltage threshold value or a current threshold value, dissipating first magnetic resonance imaging (MRI) induced energy from the means for supplying the first voltage, wherein the means for dissipating the first MRI induced energy is coupled between the means for supplying the first voltage and the means for providing the ground, and
means for dissipating second MRI induced energy from the means for supplying the second voltage, wherein the means for dissipating the second MRI induced energy is coupled between the means for supplying the second voltage and the means for providing the ground, the means for dissipating second MRI induced energy being different than the means for dissipating the first MRI induced energy.

28. The system of claim 27, further comprising:
means for generating stimulation pulses from the first electronic module; and
means for delivering the stimulation pulses from the second electrical module for neurostimulation therapy.

29. An implantable electronic device, the device comprising:
a housing;
at least one connector coupled to the housing and configured to at least one of receive first electrical signals or transmit second electrical signals;
an integrated circuit disposed within the housing, wherein the integrated circuit comprises at least one clamp stage coupled to a supply line of the integrated circuit, and wherein the at least one clamp stage is configured to dissipate magnetic resonance imaging (MRI) induced energy from the supply line in response to at least one of a voltage or a current on the supply line exceeding a respective predetermined voltage threshold value or a current threshold value; and
an electrostatic discharge (ESD) protection circuitry, wherein the ESD protection circuitry is coupled in parallel to the at least one clamp stage, wherein the ESD protection circuitry comprises a diode disposed between a bond pad and the supply line, and wherein the diode is reversely biased during normal operation of the device.

30. The device of claim 29, wherein the at least one clamp stage is configured as a shunt regulator.

31. The device of claim 29, wherein the at least one clamp stage comprises one or more high voltage metal-oxide-semiconductor field-effect transistor (MOSFET) transistors.

32. An implantable electronic device, the device comprising:
- a housing;
- at least one connector coupled to the housing and configured to at least one of receive first electrical signals or transmit second electrical signals; and
- an integrated circuit disposed within the housing, wherein the integrated circuit comprises at least one clamp stage coupled between a first supply line of the integrated circuit and a second supply line, the second supply line having a second voltage different than a first voltage of the first supply line, and wherein the at least one clamp stage is configured to dissipate magnetic resonance imaging (MRI) induced energy from the first supply line in response to at least one of a voltage or a current on the supply line exceeding a respective predetermined voltage threshold value or current threshold value.

33. The device of claim 32, wherein the at least one clamp stage is configured as a shunt regulator.

34. An implantable electronic device, the device comprising:
- a housing;
- at least one connector coupled to the housing and configured to at least one of receive first electrical signals or transmit second electrical signals; and
- an integrated circuit disposed within the housing., wherein the integrated circuit comprises at least one clamp stage coupled to a supply line of the integrated circuit, wherein the at least one clamp stage is configured to dissipate magnetic resonance imaging (MRI) induced energy from the supply line in response to at least one of a voltage or a current on the supply line exceeding a respective predetermined voltage threshold value or a current threshold value, wherein the integrated circuit is configured to enter a safe mode upon receiving a supplied voltage exceeding a threshold voltage, and wherein the integrated circuit is configured to exit the safe mode only upon receiving an exit key from a main electronic device.

35. The device of claim 34, wherein the at least one clamp stage is activated during the safe mode, and wherein the at least one clamp stage is deactivated in response to exiting the safe mode.

* * * * *

UNITED STATES PATENT AND TRADEMARK OFFICE
CERTIFICATE OF CORRECTION

PATENT NO. : 9,744,352 B2
APPLICATION NO. : 14/952848
DATED : August 29, 2017
INVENTOR(S) : Tol et al.

It is certified that error appears in the above-identified patent and that said Letters Patent is hereby corrected as shown below:

Column 31, Line 43: "or transmit second electfical" should read --or transmit second electrical--

Signed and Sealed this
Second Day of January, 2018

Joseph Matal
*Performing the Functions and Duties of the*
*Under Secretary of Commerce for Intellectual Property and*
*Director of the United States Patent and Trademark Office*